(12) United States Patent
Yuen

(10) Patent No.: US 11,647,931 B2
(45) Date of Patent: May 16, 2023

(54) PHYSIOLOGICAL SIGNAL COLLECTION APPARATUS AND PERFORMANCE MONITORING APPARATUS INCORPORATING SAME

(71) Applicant: Dayton Technologies Limited, Hong Kong (HK)

(72) Inventor: Paul Anthony Yuen, Hong Kong (HK)

(73) Assignee: Dayton Technologies Limited, Hong Kong (HK)

( * ) Notice: Subject to any disclaimer, the term of this patent is extended or adjusted under 35 U.S.C. 154(b) by 691 days.

(21) Appl. No.: 16/368,895

(22) Filed: Mar. 29, 2019

(65) Prior Publication Data

US 2019/0298203 A1  Oct. 3, 2019

(30) Foreign Application Priority Data

Mar. 29, 2018 (HK) .................................. 18104351.5

(51) Int. Cl.
*A61B 5/00* (2006.01)
*A61B 5/24* (2021.01)
(Continued)

(52) U.S. Cl.
CPC ................ *A61B 5/25* (2021.01); *A61B 5/274* (2021.01); *A61B 5/6823* (2013.01); *A61B 5/6831* (2013.01)

(58) Field of Classification Search
CPC ................ A61B 5/6804; A61B 5/0408; A61B 2562/0214; A61B 2562/125;
(Continued)

(56) References Cited

U.S. PATENT DOCUMENTS

2005/0096556 A1* 5/2005 Hsieh Chen ....... A61B 5/02438
600/509
2007/0093707 A1   4/2007 Noguchi
(Continued)

FOREIGN PATENT DOCUMENTS

| CN | 105286106 A | 2/2016 |
| EP | 0966917 A1 | 12/1999 |
| WO | 2011083441 A1 | 7/2011 |

OTHER PUBLICATIONS

International Search Report for PCT/IB2020/052995 dated Jul. 24, 2020.
(Continued)

*Primary Examiner* — Adam Z Minchella

(57) ABSTRACT

A physiological signal collection electrode comprising a signal collection portion, a signal output terminal and a signal transmission portion interconnecting the signal collection portion and the signal output terminal, wherein the signal collection portion comprises a signal collection pad and the signal transmission portion comprises a signal transmission pad, wherein the signal collection portion and the signal transmission portion are integrally formed into an elongate and conductive electrode pad which extends in a longitudinal direction along a longitudinal axis; wherein the signal collection portion has a signal collection surface for making abutment contact with a signal surface and the signal collection surface is parallel to the longitudinal axis; and wherein the signal output terminal is parallel to the signal collection surface, extends transversely to the longitudinal axis and protrudes above the signal collection surface.

20 Claims, 11 Drawing Sheets

(51) Int. Cl.
*A61B 5/25* (2021.01)
*A61B 5/274* (2021.01)

(58) Field of Classification Search
CPC ........ A61B 2562/182; A61B 2562/227; A61B 18/1442; A61B 18/1402; A61B 2018/1405; A61B 2018/1412; A61B 2018/1427; A61B 2018/1462; A61B 2018/1495; A61B 2018/146; A61B 18/1445; A61B 2018/1455
See application file for complete search history.

(56) References Cited

U.S. PATENT DOCUMENTS

| | | | |
|---|---|---|---|
| 2007/0285868 A1* | 12/2007 | Lindberg | A61B 5/24 |
| | | | 600/382 |
| 2008/0139892 A1* | 6/2008 | Juan | A61B 5/6831 |
| | | | 600/300 |
| 2008/0177168 A1 | 7/2008 | Callahan et al. | |
| 2013/0123601 A1 | 5/2013 | Lindberg et al. | |
| 2013/0131460 A1* | 5/2013 | Yuen | A61B 5/6831 |
| | | | 600/382 |
| 2013/0158380 A1 | 6/2013 | Okuda et al. | |
| 2016/0058375 A1* | 3/2016 | Rothkopf | G04G 17/02 |
| | | | 600/323 |

OTHER PUBLICATIONS

Extended European Search Report of counterpart European Patent Application No. 20785028.0 dated April 20, 2022.

* cited by examiner

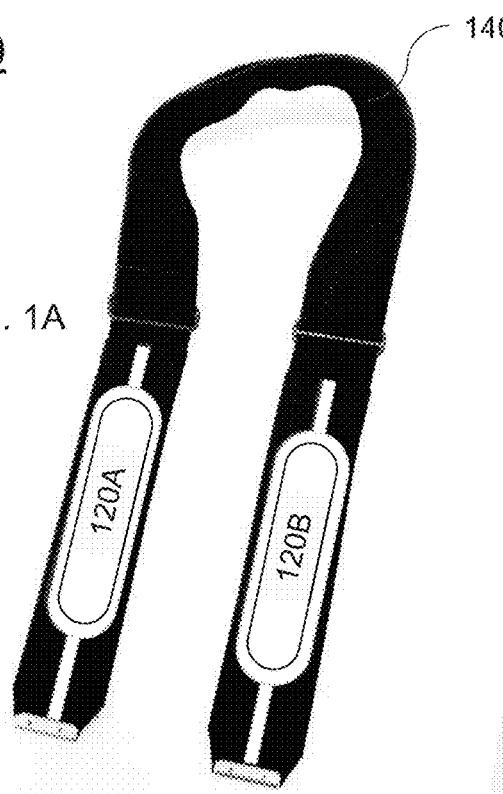
Fig. 1A
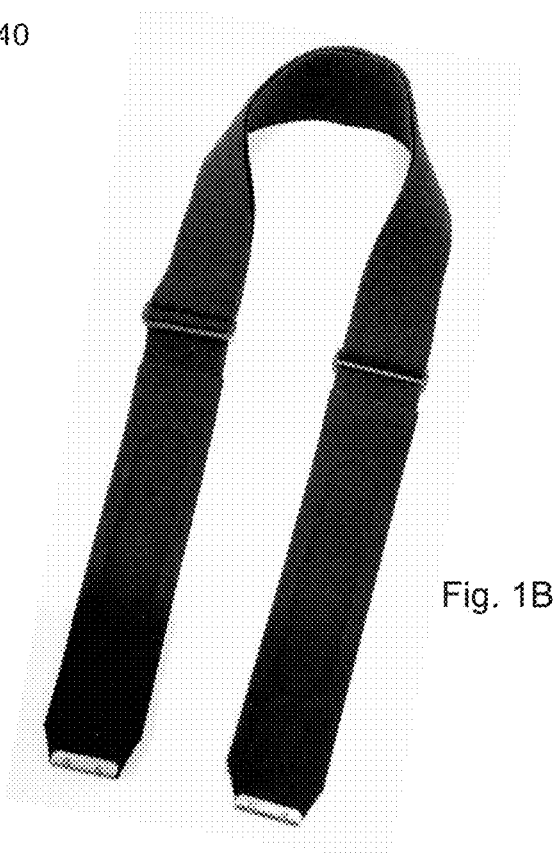
Fig. 1B
Fig. 1C
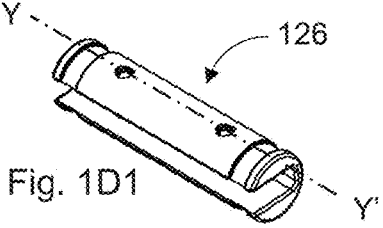
Fig. 1D1
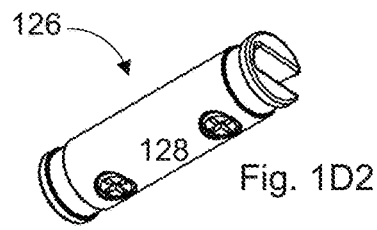
Fig. 1D2
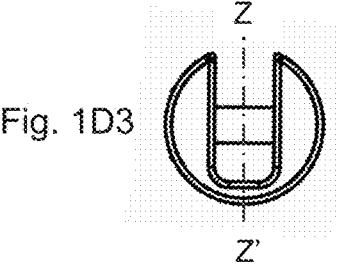
Fig. 1D3

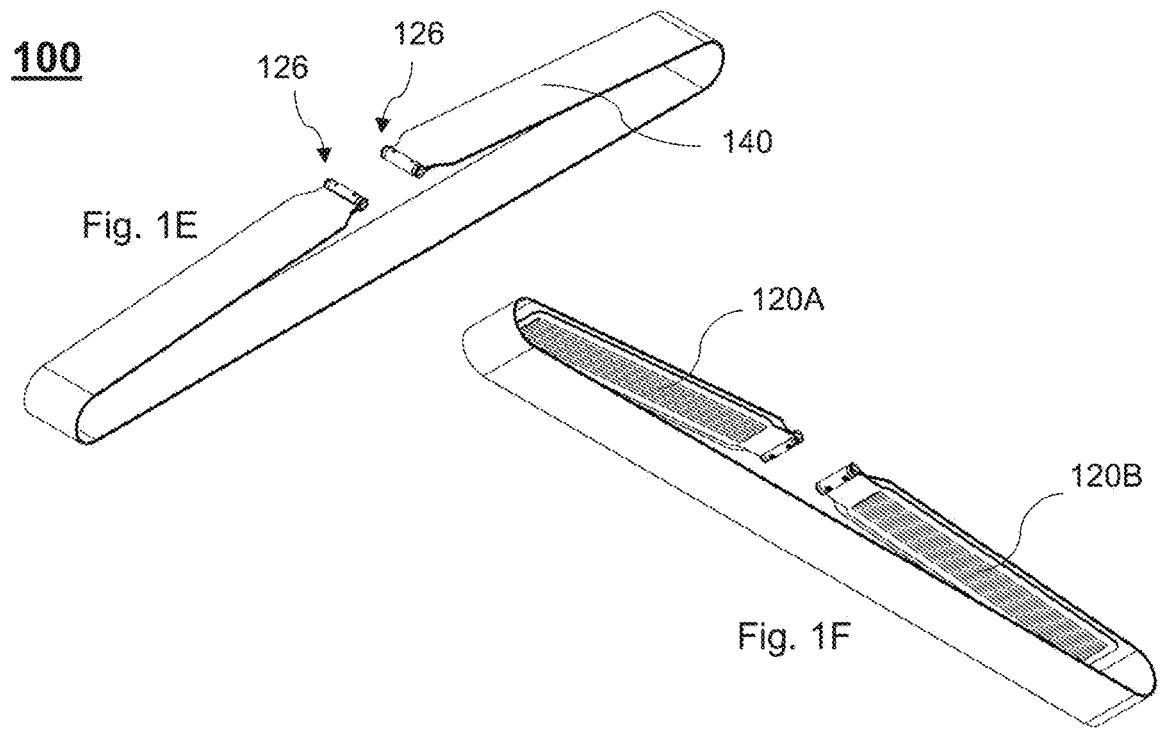
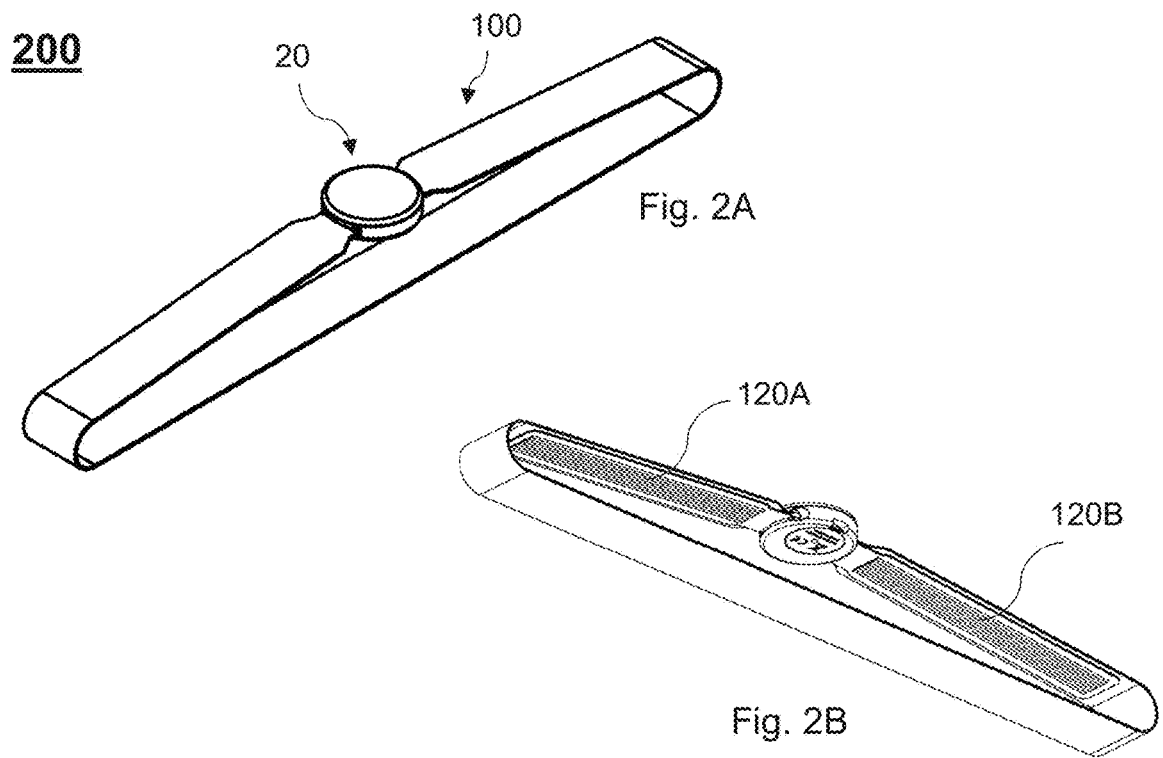

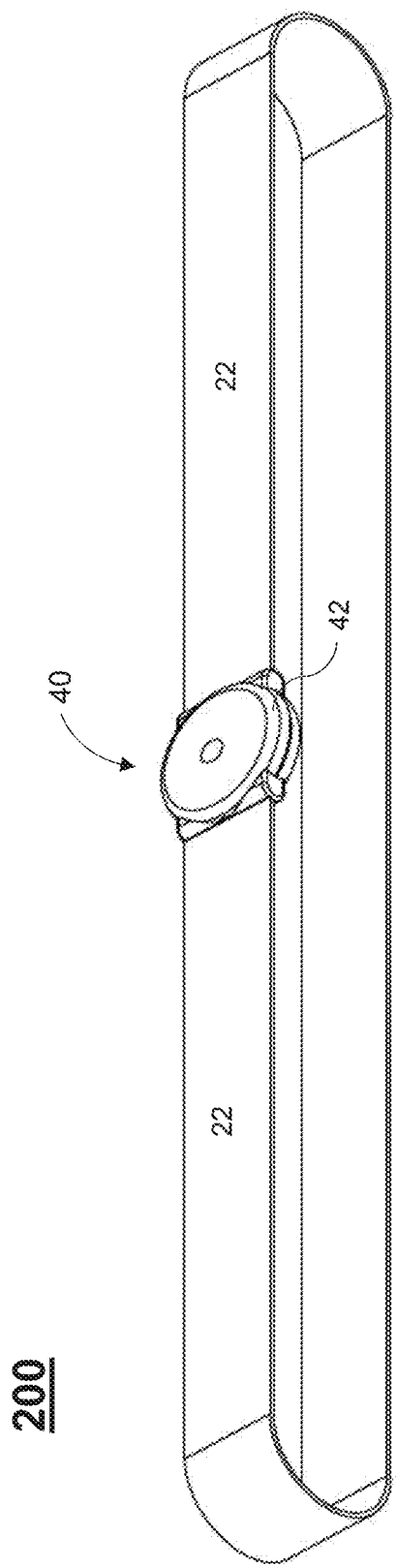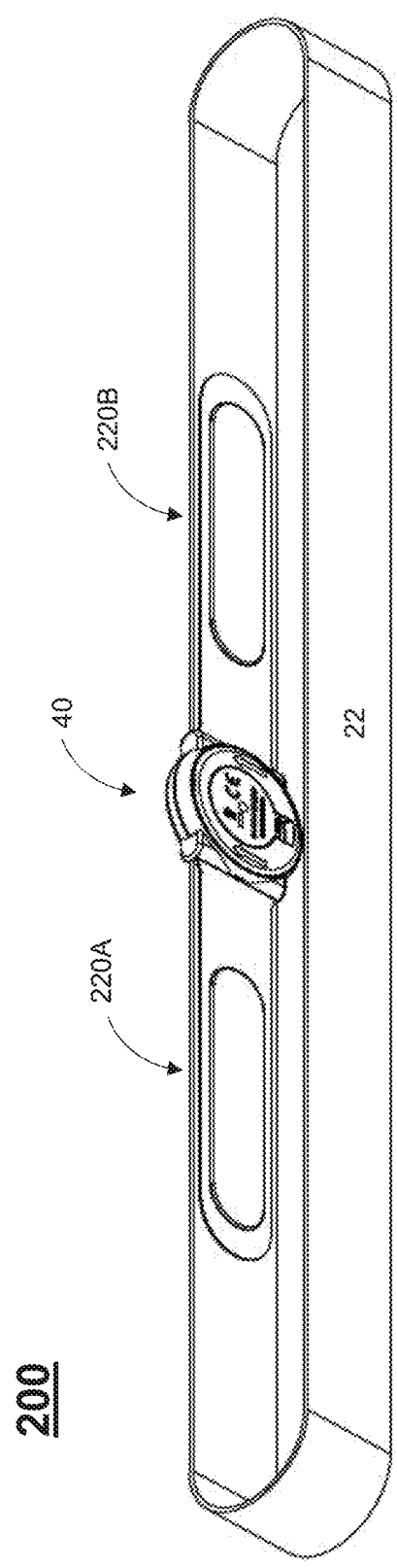

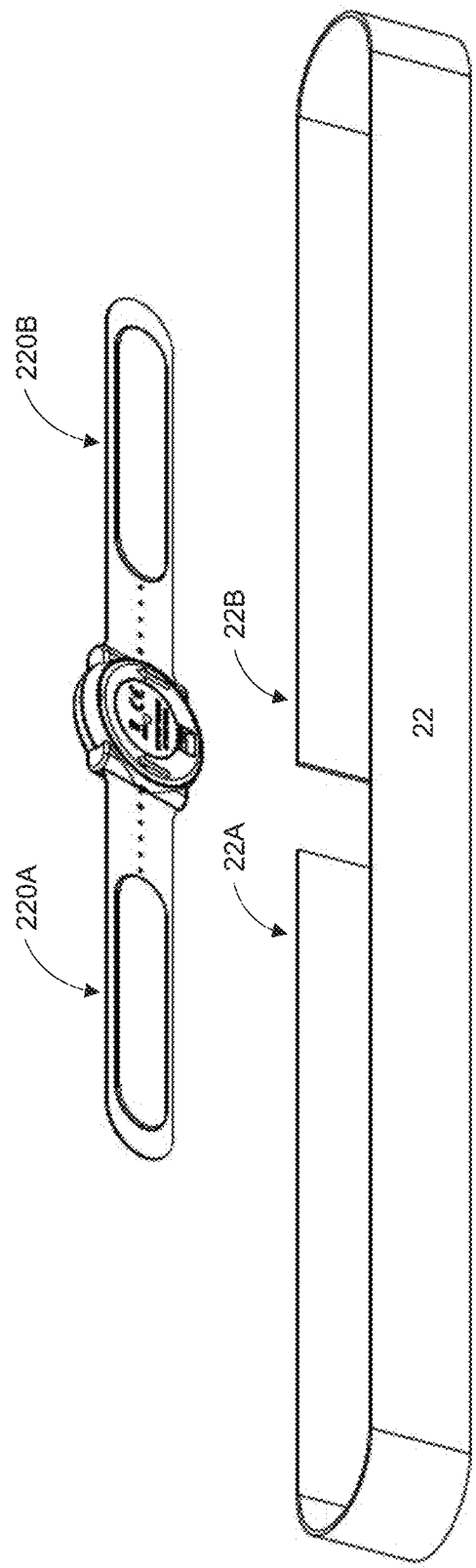
Fig. 5C1
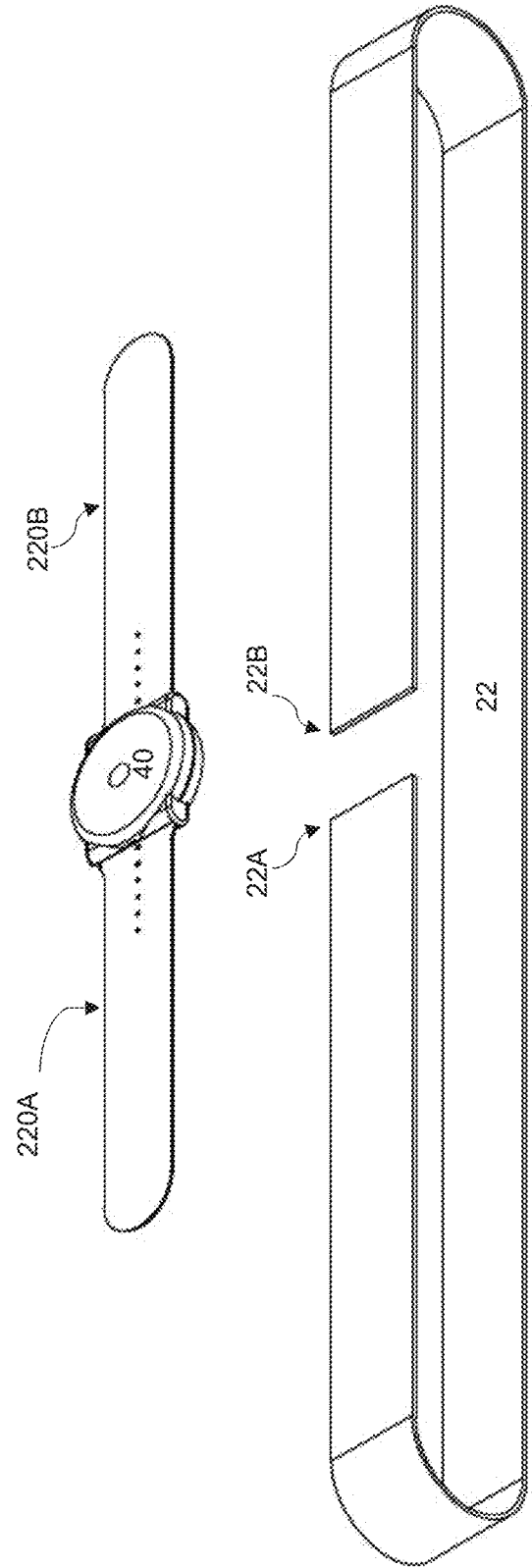
Fig. 5C2

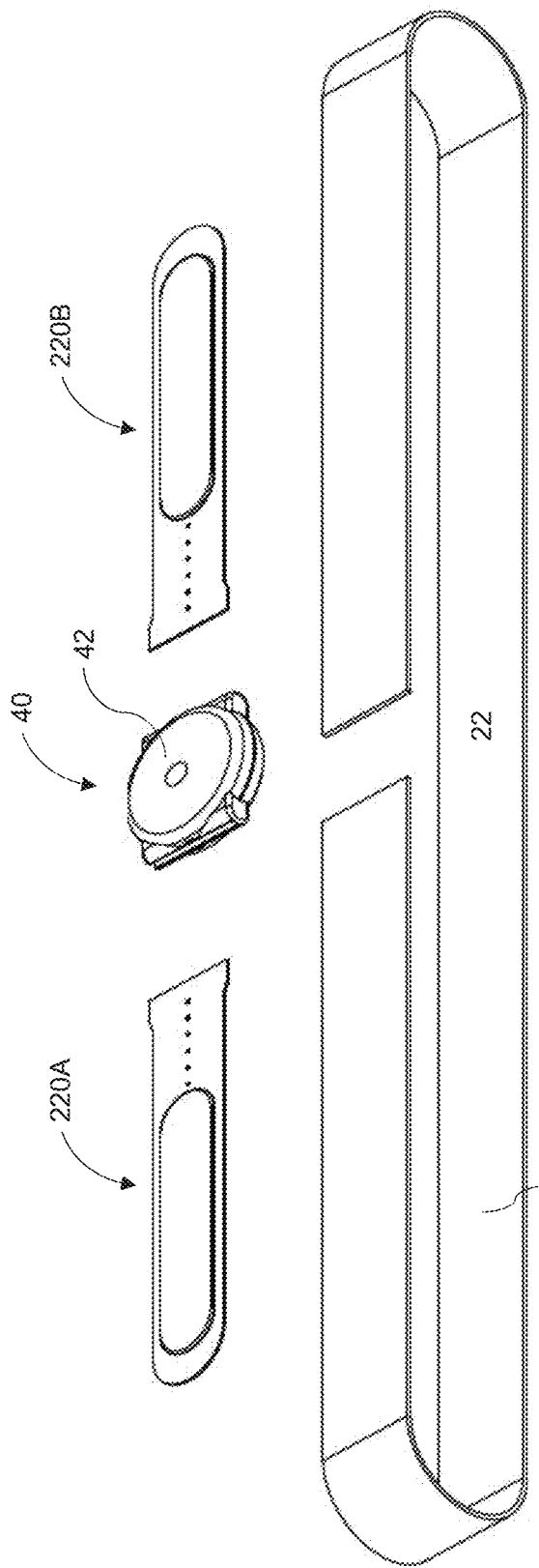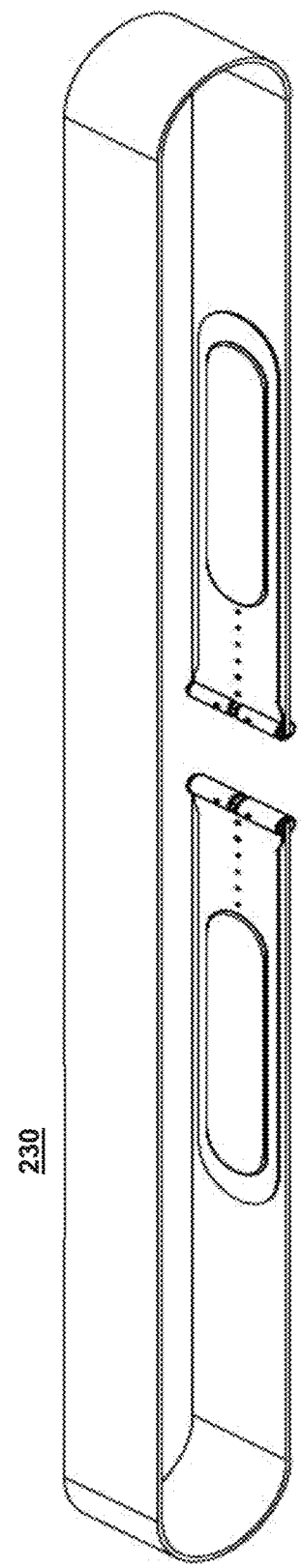

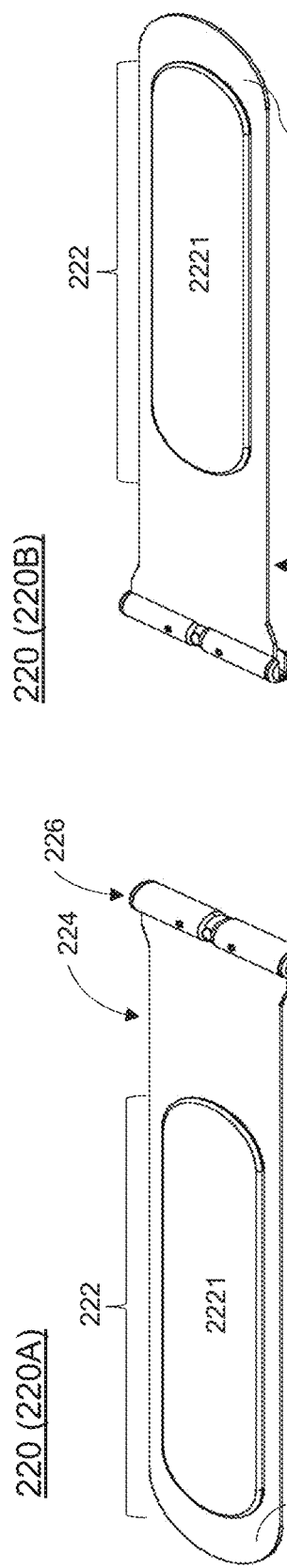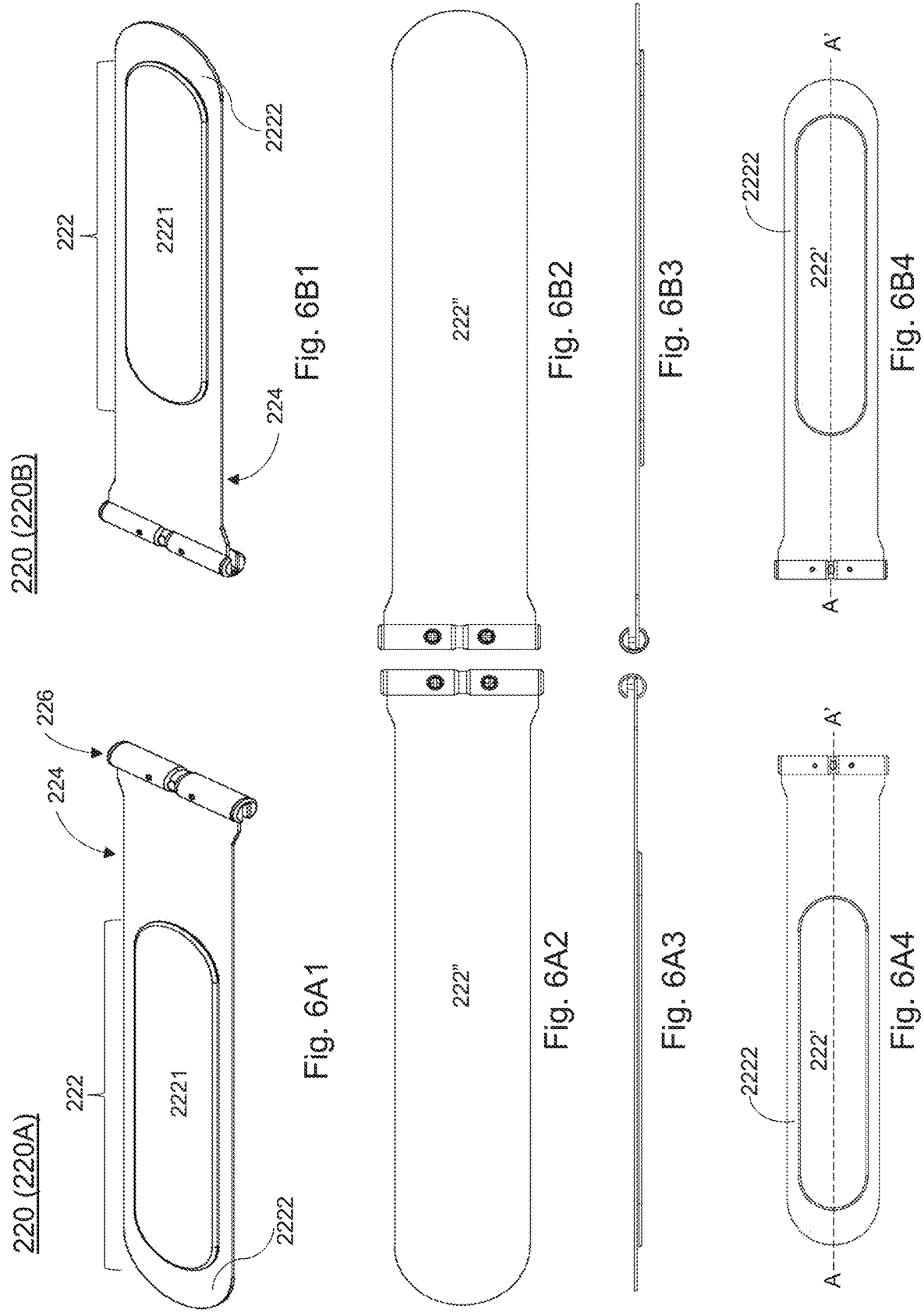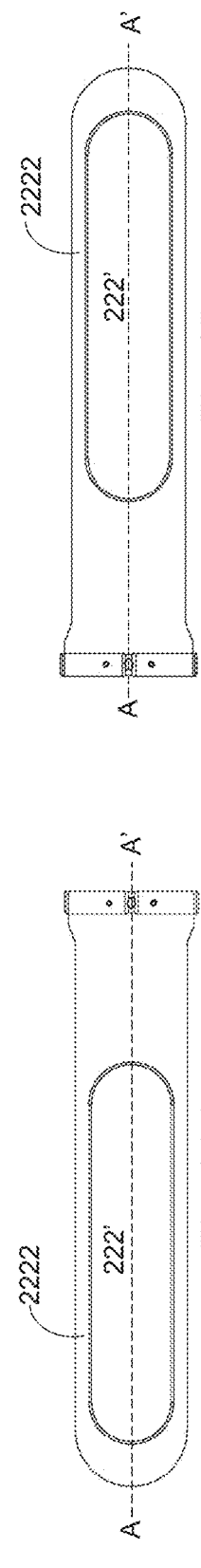

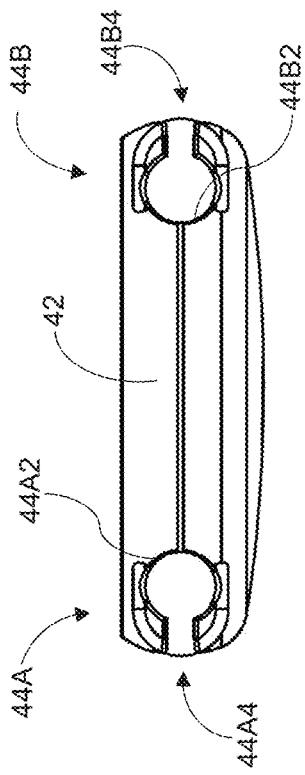
Fig. 7A2
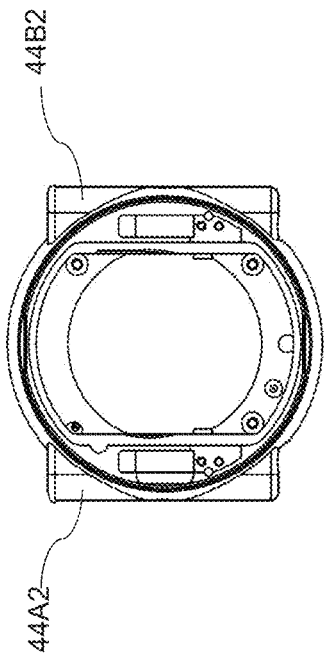
Fig. 7A4
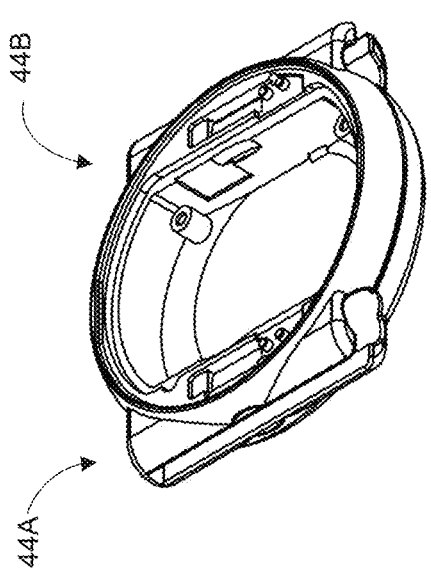
Fig. 7A1
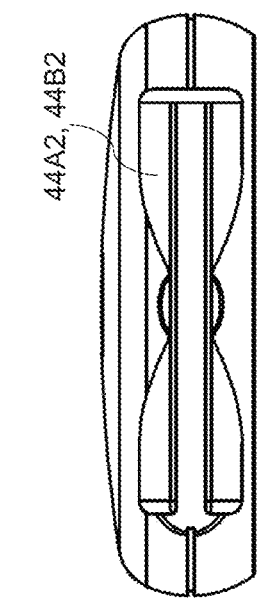
Fig. 7A3

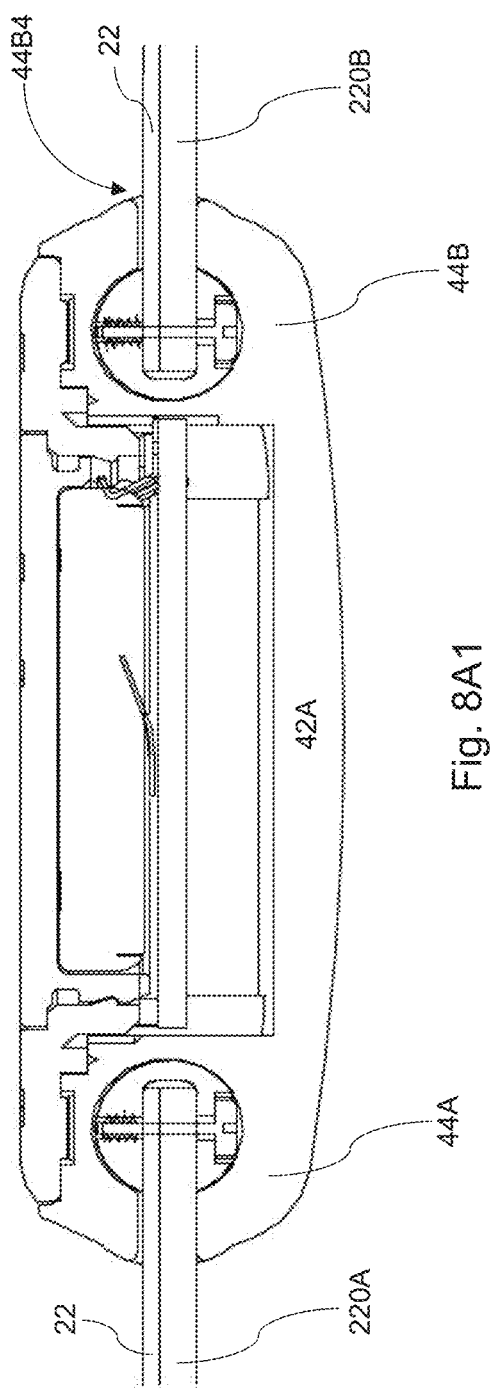
Fig. 8A1
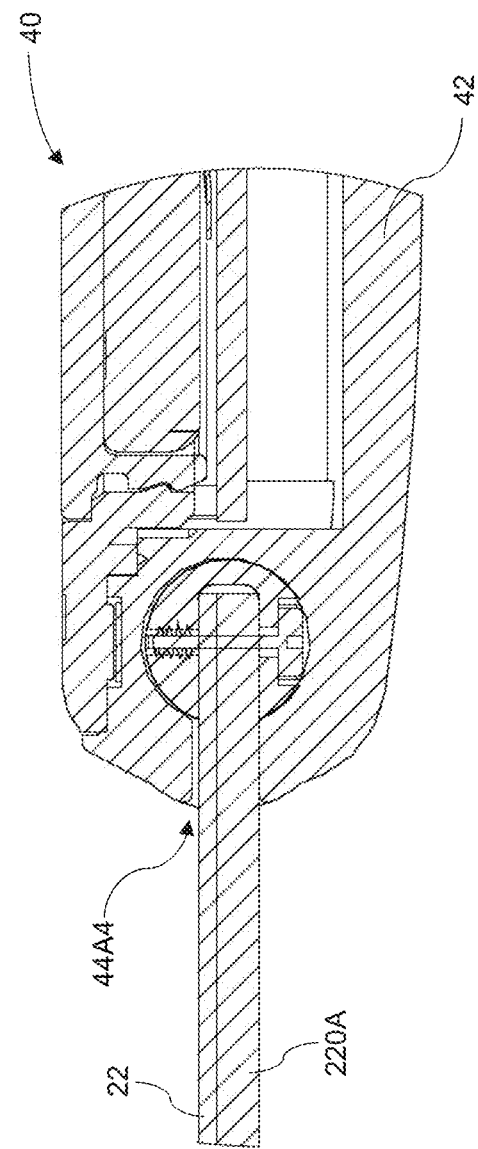
Fig. 8A2

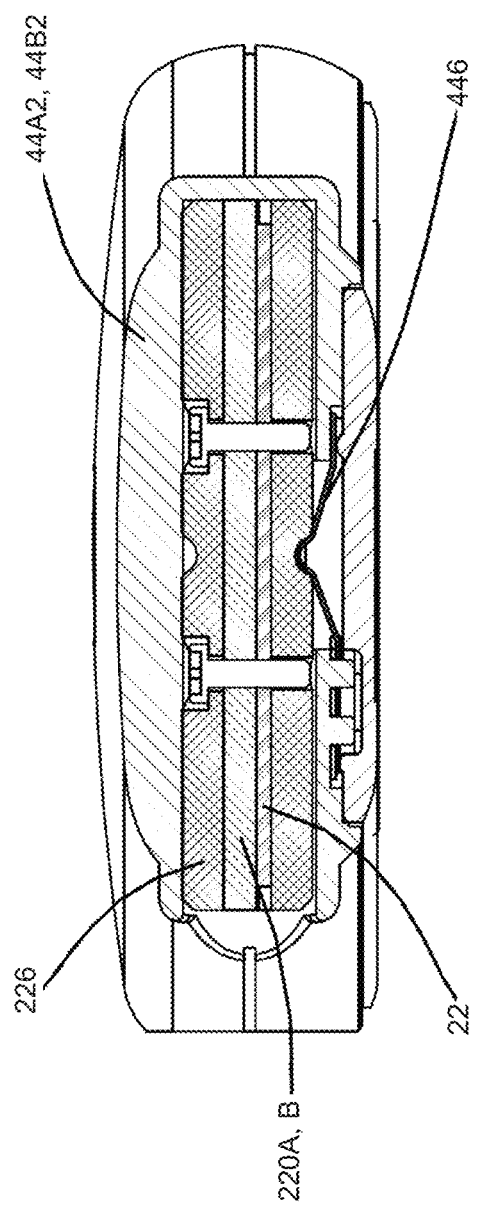

PHYSIOLOGICAL SIGNAL COLLECTION APPARATUS AND PERFORMANCE MONITORING APPARATUS INCORPORATING SAME

CROSS REFERENCE TO RELATED APPLICATIONS

The present application claims the benefit of Hong Kong Patent Application No. 18104351.5 filed on Mar. 29, 2018, the contents of which are incorporated herein by reference in its entirety.

FIELD

The present disclosure relates to physiological signal collection apparatus, and more particularly to chest-worn physiological signal collection apparatus. This invention also relates to performance monitoring apparatus comprising a physiological signal collector and a signal processing device for processing collected physiological signals. More specifically, although not solely limited thereto, the present invention also relates to chest-worn swim monitors.

BACKGROUND

Physiological signal collectors are useful for collecting physiological data of a person during physical exercises, during medical examination or during everyday life. Typical physiological signals which are commonly collected for processing and analyzing include ECG, heart rate, blood pressure, blood oxygen content, body temperature. The collected signals are typically processed and converted into data which provide information on the state of health, physical fitness, or physical performance of a person.

A chest strap is a known type of physiological signal collectors adapted to be chest-worn by a person for collecting physiological signals during physical exercises or activities. Physiological signals commonly collected by a chest strap include, for example, heart-rate, ECG pulses, skin conductivity, infra-red absorption or other electrical or opto-electrical signals measurable from the skin of a person.

A typical chest strap usually includes a plurality of electrodes or sensors which is mounted on a flexible plastic chest strap in a spaced apart manner to collect weak physiological signals in electrical or optical form from a human body for differential signal processing. Each electrode typically comprises a signal reception pad having a signal reception surface with a surface area large enough to collect signals which are strong enough for processing by a signal processing device, such as a heart rate signal processor.

The flexible plastic strap is usually a pre-assembled strap which comprises a length adjustment or tension adjustment arrangement to tighten the strap against the body of a person, usually the chest, during use to provide electrical contact between the electrodes and the skin of a user. The strap is usually made of soft plastics to provide flexibility for body wearing and electrical insulation between the electrodes. The tensions adjustment arrangement typically comprises a length of soft plastic strap portion which runs around buckle or clasp arrangements.

It would be advantageous to provide improvement chest straps to mitigate shortcomings of conventional chest straps.

SUMMARY

There is disclosed an ECG signal collection electrode. The ECG signal collection electrode comprises a signal collection portion, a signal output portion and a signal transmission portion interconnecting the signal collection portion and the signal output portion; wherein the signal collection portion comprises an elongate signal collection pad, the signal transmission portion comprises an elongate signal transmission pad, and the signal output portion comprises an elongate metallic signal output terminal; wherein the signal collection pad and the signal transmission pad are integrally molded of a flexible conductive and moldable material to form an elongate and flexible conductive pad; wherein the flexible conductive pad extends along a longitudinal axis and the signal output terminal extends transversely to the longitudinal axis, the longitudinal axis defining a longitudinal direction; wherein the signal transmission pad has an input end which is in abutment with the signal collection pad and an output end which is a free end distal from the input end; and wherein the signal output terminal extends along the output end of the signal transmission pad and is in continuous physical and electrical abutment contact with the output end as it extends along the output end of the signal transmission pad.

There is also disclosed an ECG signal collection apparatus comprising a strap having longitudinal free ends and ECG signal collection electrodes. The strap comprises a first longitudinal free end and as a second longitudinal free end, the second longitudinal free end being distal to the first longitudinal free end. The ECG signal collection electrodes comprises a first ECG signal collection electrode which is mounted on the first longitudinal free end and a second ECG signal collection electrode which is mounted on the second longitudinal free end, wherein at least one of the first ECG signal collection electrode and the second ECG signal collection electrode is an ECG signal collection electrode according to any of the claims.

There is also disclosed a physiological signal apparatus comprising an ECG signal collection apparatus according to any claim and an electronic apparatus. The electronic apparatus comprises a housing and signal input receptacles on the housing, wherein the signal input receptacles are adapted for closely fitted reception of the signal output terminals of the first ECG signal collection electrode and the second ECG signal collection electrode, and wherein each one of the signal input receptacles comprises a signal input terminal exposed inside the signal input receptacles such that when the signal output terminals of the first ECG signal collection electrode and the second ECG signal collection electrode are securely received inside the signal input receptacles, a signal transfer path from the ECG signal collection apparatus and the electronic apparatus is formed to facilitate transfer of collected physiological signals to the electronic apparatus.

BRIEF DESCRIPTION OF THE DRAWINGS

The disclosure will be described by way of example and with reference to the accompanying Figures, in which:

FIGS. 1A and 1B are, respectively, top plan view and bottom plane view of a signal collection apparatus 100 in a partially folded configuration according to the disclosure, FIG. 1C is a bottom plan view of the signal collection apparatus 100 in a spread configuration, FIGS. 1D1 and 1D2 are perspective views of an example signal output terminal 126 of the example signal collection apparatus 100, FIG. 1D3 is an end view of the signal output terminal 126 viewed from one longitudinal end, FIGS. 1E and 1F are perspective views of the signal collection apparatus 100 in a partially looped configuration, FIGS. 2A and 2B are perspective views of a physiological signal apparatus 200 according to the disclosure, FIGS. 5A and 5B are perspective views of a physiological signal monitoring assembly comprising a signal collection apparatus and a strap-ends connector of the present disclosure, FIGS. 5C1 and 5C2 are partially exploded perspective views of the assembly of FIG. 5A showing the strap and the signal collection apparatus, FIG. 5C3 is a perspective view with major parts of the signal collection apparatus of FIGS. 5C1 and 5C2 further exploded, FIG. 5C4 is a perspective view showing a pair of electrodes fixed on the strap;

FIGS. 6A1, 6A2, 6A3 and 6A4 are various views of the first signal collection electrode of the assembly of FIG. 5A, FIGS. 6B1, 6B2, 6B3 and 6B4 are various views of the second signal collection electrode of the assembly of FIG. 5A, FIGS. 7A1, 7A2, 7A3 and 7A4 are various views showing a portion of the main housing and the anchoring terminal housings, FIG. 8A1 is a schematic side view taken along the longitudinal direction of the signal output terminal in the region of the electronic device, FIG. 8A2 is an enlarged cross-sectional view of a portion of FIG. 8A1, and FIG. 8A3 is a cross-sectional view showing anchoring relationships between the signal collection apparatus and the main housing of the electronic device taken along the longitudinal direction of the strap.

DETAILED DESCRIPTION

Figure 2C:
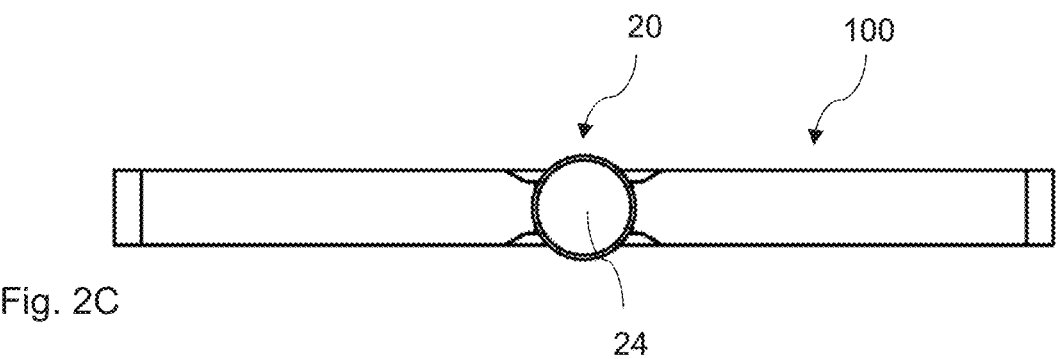
FIGS. 2C and 2D are, respectively, top plan and side views of the example physiological signal apparatus 200.
Figure 2D:
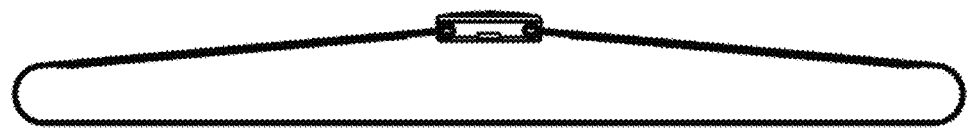

An example signal collection apparatus comprises a strap and a pair of example physiological signal collection electrodes mounted on the strap. The example physiological signal collection electrodes of the example signal collection apparatus 100 comprise a pair of ECG signal collection electrodes 120A, 120B and the ECG signal collection electrodes are mounted on longitudinal ends of a flexible strap 140, as depicted in FIGS. 1A and 1B. The example signal collection apparatus 100 is adapted for wearing on a living body for collection of ECG signals from the chest cage of the living body when the apparatus is worn on the living body and the strap is configured as a chest strap suitable for attaching the physiological signal collection electrodes to the chest of the living body. The living body is also referred to herein as a user or a wearer.

The example flexible strap 140 is elongate, has a longitudinal axis X-X' which defines a longitudinal direction, and extends between a first longitudinal end and a second longitudinal end. The signal collection apparatus 100 is configurable between a partially folded configuration of FIGS. 1A and 1B and a spread configuration of FIG. 1C. In the spread configuration of FIG. 1C, the signal collection apparatus 100 is substantially linear and the longitudinal axis X-X' is substantially a straight line. In the partially looped configuration of FIGS. 1A and 1B, the signal collection apparatus 100 follows the shape (or more exactly, the random shape) of the flexible strap.

The example flexible strap is elastic or resilient and is resiliently stretchable between a first length which is a neutral, un-tensioned, length of the strap when the strap is under no longitudinally applied stretching tension and a second length which is an extended length when the strap is under a longitudinally applied stretching tension. The second length is longer than the first length, which is an unstretched, neutral, length of the strap. The flexible strap may be formed from an elastomeric material. Example elastomeric material suitable for forming the flexible and elastic strap include or example, from Spandex, Lycra or elastane, and for example, by weaving. In some embodiments, the chest strap is formed by a combination of stretchable and non-stretchable strap portions without loss of generality.

The ECG signal collection electrodes comprise a first ECG signal collection electrode 120A and a second ECG signal collection electrode 120B. The first ECG signal collection electrode 120A and the second ECG signal collection electrode 120B are on opposite longitudinal ends of the strap 120. As depicted in the Figures, the first ECG signal collection electrode is mounted on the first longitudinal end of the flexible strap and the second ECG signal collection electrode is mounted on the second longitudinal end of the flexible strap. The first ECG signal collection electrode and the second ECG signal collection electrode collectively form a pair of ECG signal collection electrodes each having a signal collection surface for ECG signal collection.

When in example use, the signal collection apparatus 100 is worn on the body of a wearer such that the signal collection surfaces of the first and second signal collection electrodes are in physical abutment and electrical contact with the chest, and more particularly the left and right chest cages, of the wearer. When the signal collection apparatus 100 is in use and worn on a user, the signal collection apparatus 100 is formed into a closed loop, for example, formed into a loop when in cooperation with an electronic apparatus, for example, a signal transmission apparatus or a signal processing apparatus, which is attached to the longitudinal ends of the signal collection apparatus 100, as depicted in FIGS. 2A and 2B.

The length of the strap 140 is adjustable, selectable and/or customized so that when the signal collection apparatus 100 is duly worn, the tension, for example, stretching tension, present in the strap will operate to urge the first and second signal collection electrodes inwardly towards the body of the wearer so that the signal collection surfaces of the first and second signal collection electrodes are urged towards and are in compressive contact with the skin of the wearer. To facilitate effective ECG signal collection, the first and second signal collection electrodes are positioned such that their signal collection surfaces are respectively on the left and right chest cage portions of the wearer.

In this example, the first and second signal collection electrodes are identical ECG signal collection electrodes. Each one of the first and second signal collection electrodes is an ECG signal collection electrode comprising a signal collection portion, a signal output portion and a signal transmission portion interconnecting the signal collection portion and the signal output portion.

The ECG signal collection electrode 120A, 120B is elongate and extends along a longitudinal axis which defines a longitudinal direction. When the ECG signal collection electrode 140A, 140B is mounted on the strap, the longitudinal axis of the ECG signal collection electrode 140A, 140B and the longitudinal axis X-X' of the flexible strap are aligned or co-axial.

The signal collection portion of the ECG signal collection electrode comprises a signal collection pad 122. The signal collection pad is elongate and comprises a signal collection surface 122A and a back surface which is parallel to the signal collection surface, but opposite facing. The distance between the signal collection surface and the back surface defines the thickness of the signal collection pad. The signal collection surface has a signal collection area and the signal collection area is devised so that ECG signals of a sufficiently large signal amplitude will be collected when in use. In this example, the signal collection surface has a signal collection area of approximately 15 square centimeters ($cm^2$), measuring 8 cm (length) and 1.9 cm (width) with rounded longitudinal ends. In general, a signal collection surface of between 9-25 square centimeters ($cm^2$) would be useful and the signal collection surface may have a length of between 6-10 cm and a width of between 1.5-2.5 cm.

The signal collection pad includes a signal output end at a longitudinal end and the signal transmission portion is in abutment with the signal collection pad at the signal output end of the signal collection pad. The signal collection surface 122A is also referred to as an upper surface and the back surface is referred to as a lower surface for ease of reference.

The signal transmission portion of the ECG signal collection electrode comprises a signal transmission pad 124. The signal transmission pad is elongate and forms a conductive bridge which extends from the signal collection surface to connect the signal output terminal and the signal collection portion, or more specifically, to connect the signal output end of the signal collection portion and the signal output terminal. The signal transmission pad includes an upper surface which is on the same side as the upper surface of the signal collection pad and a lower surface which is on the same side as the lower surface of the signal collection pad.

Both the signal collection pad and the signal transmission pad extend along the longitudinal axis X-X' and have the longitudinal axis X-X' as their center axes. In other words, the signal collection pad and the signal transmission pad have a common center axis. In this example, both the signal collection pad and the signal transmission pad are laterally symmetrical about their respective center axis, which is the common axis. In some embodiments, the signal collection pad and/or the signal transmission pad are not laterally symmetrical or may not have a common center axis without loss of generality.

The signal output terminal 126 is an elongate conductive member which is to function as a distributed signal output terminal. The signal output terminal is regarded as a distributed output since it has a signal output area which is comparable to the cross-sectional area of the signal output end of the signal transmission pad or the cross-sectional area of the signal output end of the signal collection pad. The cross-sectional area is measured in a direction transversal to the longitudinal axis of the signal collection pad and/or the signal transmission pad.

The elongate signal output terminal 126 extends along a longitudinal axis Y-Y' to define its length. The longitudinal axis Y-Y' is orthogonal or substantially orthogonal to the longitudinal axis X-X'. In other words, the elongate signal output terminal 126 extends a transverse direction which is transverse to the longitudinal direction defined by the longitudinal axis X-X'.

Referring to FIGS. 1D1, 1D2 and 1D3, the example signal output terminal 126 comprises a conductive main body 128 which extends along the longitudinal axis Y-Y'. The conductive main body is an elongate body having an interior compartment and an entry aperture which defines an entry into the interior compartment. The interior compartment is defined by an interior wall (or an interior boundary wall) which also defines the entry aperture. The interior wall extends along the transverse direction to define an elongate entry aperture and an elongate interior compartment. The interior compartment is a receptacle compartment for fitted or (closely fitted) reception of the output end of the signal transmission pad and is formed as a through slot which extends through the main body. The through slot extends along a slot axis which is parallel to the longitudinal axis Y-Y' of the signal output terminal 126. The main body has a generally C-shaped or U-shaped cross-section, with the entry aperture at the opening portion of the C-shaped or U-shaped cross-section. The entry aperture and/or the interior slot is/are shaped and/or dimensioned for fitted (or closely fitted) reception of the output end of the signal transmission pad. To facilitate fitted (or optionally closely fitted) reception of the output end of the signal transmission pad, the entry aperture and/or the interior slot has a transversal clearance which is comparable or slightly smaller than the thickness of the output end of the signal transmission pad. The transversal clearance of the entry aperture and/or the interior slot is measured in a direction (the transverse direction) which is orthogonal to the longitudinal direction (or overall longitudinal direction) of the longitudinal direction defined by the longitudinal axis X-X'. The main body of the signal output terminal 126 is laterally symmetrical about a center axis Z-Z', and the center axis Z-Z' is orthogonal to both the X-X' and Y-Y' axes.

The signal output terminal 126 includes optional fasteners for securing or fastening the main body 128 with the signal transmission pad, and corresponding fastener bores for receiving the fasteners. The main body has a uniform cross-section along its length, except at the fastener bores. In this example, there are two fasteners and two fastener bores. In other embodiments, there may be one fastener or more than two fasteners for securing the signal output terminal to the signal transmission pad without loss of generality. Where the signal output terminal is integrally molded with or on the signal transmission pad, there may be no need for external or additional fasteners. In this example, the example fasteners depicted in FIGS. 1D1 and 1D2 are threaded screws.

The example main body of the example signal output terminal 126 is a hollow metal bar, for example, a copper bar, an aluminum bar, a stainless-steel bar or other a bar of other metals or alloys. In some embodiments, the main body is made of a moldable material such as a conductive polymeric material, for example, carbonized rubber. For example, the main body may be formed of the same materials as the materials forming the signal collection pad and/or signal transmission pad. In some embodiments, the signal collection pad and/or signal transmission pad and/or the main body of the output terminal are integrally formed as a single flexible piece.

The main body of the example signal output terminal is shaped and dimension for closely fitted reception of the output end of the signal transmission pad. To facilitate the closely fitted reception, the main body of the example signal output terminal and the output end of the signal transmission pad are a well-matched snap-fit pair, and the main body of the example signal output terminal is shaped and dimension to function as a clamp or clamping member to clamp on the output end of the signal transmission pad. As the main body of the example signal output terminal has a C-shaped cross section, the main body and/or the signal output terminal is also a C-clamp shaped electrical connector. When the C-clamp connector is attached to the signal transmission pad, the output end of the signal transmission pad is guarded, covered or protected to enhance durability.

As the main body of the example signal output terminal and the output end of the signal transmission pad are a well-matched snap-fit pair, the internal boundary wall is contiguous or abutment contact with the output end of the signal transmission pad. Since the internal boundary wall of the signal output terminal is in contiguous or abutment contact with the output end of the signal transmission pad, the internal boundary wall of the signal output terminal, which defines the entry aperture and the interior compartment, defines a distributed signal input portion of the signal output terminal. The internal boundary wall of the signal output terminal includes an upper boundary wall, a lower boundary wall and a peripheral wall interconnecting the upper and lower boundary walls. When the signal output terminal is mounted on the signal transmission pad, which effectively means when the signal output terminal is mounted on the output end of the signal transmission pad, the upper and lower surfaces on the output end of the signal transmission pad are in contiguous or abutting physical and electrical contact with the upper and lower boundary walls of the signal output terminal. When the signal output terminal is mounted on the signal transmission pad, the output end of the signal transmission pad is in compressive contact with the signal output terminal. More specifically, the output end of the signal transmission pad is compressively sandwiched between the upper and lower boundary walls. Each one of the upper and lower boundary walls is an elongate conductive wall and the upper and lower boundary walls cooperate to define an elongate, distributed signal input of the signal output terminal.

Referring to FIGS. 1A and 1B, the first ECG signal collection electrode 120A is mounted on a first longitudinal end of the strap 140 and the second ECG signal collection electrode 120A is mounted on the second longitudinal end of the strap 140. The first and second longitudinal ends of the strap 140 are opposite longitudinal ends, or more exactly opposite longitudinal free ends, of the strap 40, and the distance between the first and second longitudinal ends of the strap 140 defines the length of the strap or the signal collection apparatus 100. In this example, the ECG signal collection electrodes 120A, 120B are attached to the strap 140, for example, by gluing such as hot-melt glue or hot-melt gluing or other permanent attachment means.

The ECG signal collection electrodes 120A, 120B are disposed such that the main bodies of the respective output terminals of the signal output terminals form the free longitudinal ends of the apparatus 100.

Figure 3A:
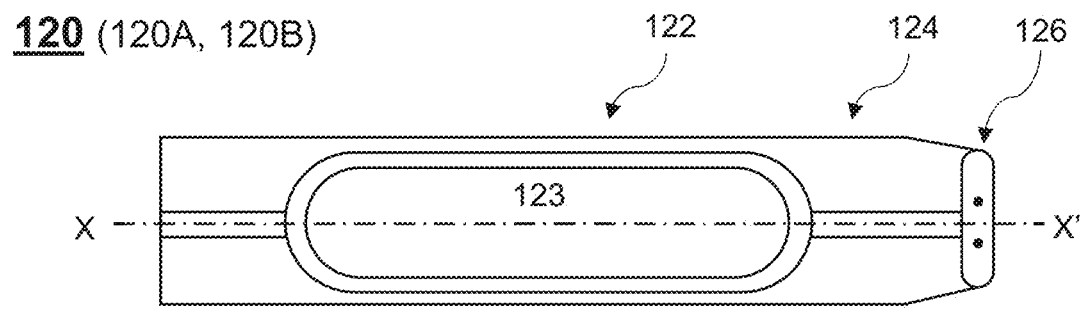
FIG. 3A is a top plan view of an example ECG signal collection electrode 120 according to the disclosure.
Figure 4A:
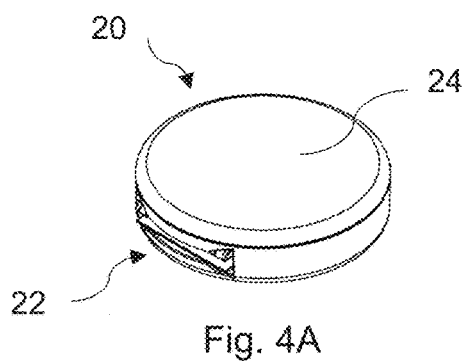
FIGS. 4A, 4B and 4C are various views of an example electronic apparatus 20 which is attachable to the signal collection apparatus 100 to form an example physiological signal apparatus 200.
Figure 4B:
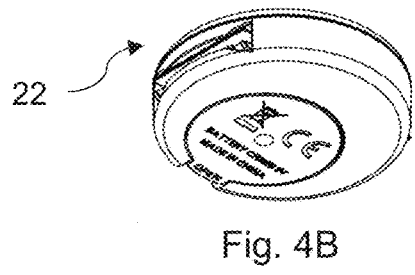
Figure 4C:
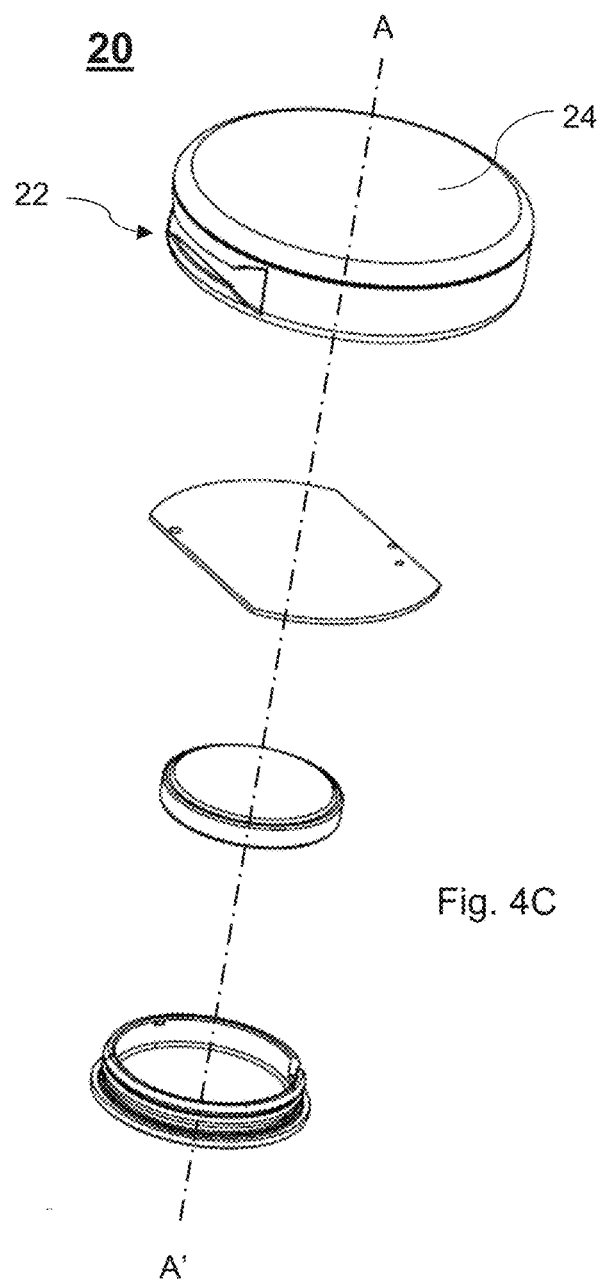

Each one of the first and second signal collection electrodes is an ECG signal collection electrode 120 comprising a signal collection portion, a signal output portion and a signal transmission portion interconnecting the signal collection portion and the signal output portion, as depicted in FIG. 3A.

The signal collection portion 122 is molded of a flexible and conductive material and comprises a base portion and a signal collection pad. The signal collection pad comprises a signal collection surface 123 which is elevated above and surrounded by the base portion. After the ECG signal collection electrode has been mounted on the strap, the elevated signal collection surface 123 projects above the surrounding base portion and surrounding strap fabrics such that when the ECG signal collection electrode is mounted on the strap, the signal collection surface 123 is exposed for skin contact with the user while the surrounding base portion is covered by a fabric surface of the strap. The strap optionally comprises a plurality of layers and the ECG signal collection electrode is retained between two adjacent fabric layers of the strap. In some embodiments, the ECG signal collection electrode is glued on an outer/inner surface of the strap and the entire signal collection portion is exposed.

The signal transmission portion is connected in series with the signal collection portion and continues longitudinally from the signal collection portion. In this example, the signal transmission portion is formed of the same material as the signal collection portion, and the signal collection portion and the signal transmission portion are integrally molded as a single flexible conductive pad. In this example, the signal collection surface 123 is also elevated above the upper surface of the signal transmission pad. The single flexible conductive pad of the integrally formed signal collection portion and the signal transmission portion has a substantially uniform thickness along its length. The example signal collection portion 122 has a substantially uniform width along its length, which is a dimension measured along the longitudinal direction X-X'. The signal transmission portion has an initial width which is equal to the width of the signal collection portion 122 and tapers to narrow as it extends towards its output end, which is an end distal to the signal collection portion. The initial width is the width of the signal transmission portion proximal the signal collection portion. In this example, the output end of the signal transmission pad is more than 50% of the initial width or the width of the signal collection surface. In some embodiments, the output end of the signal transmission pad has a width which is the same or comparable to the initial width or the width of the signal collection surface. In some embodiments, the output end of the signal transmission pad has a width which is between 50% and 100% of the initial width or the width of the signal collection surface, for example, between 40%, 45%, 50%, 55%, 60%, 65%, 70%, 75%, 80%, 85%, 90%. 95%, 100% or any range or ranged selectively defined by combining any of the aforesaid values. In this example, the signal output terminal 126 has a length which is equal to the width of the output end of the signal transmission pad. In some embodiments, the signal output terminal 126 has a length which is larger, for example slightly larger, than or smaller, for example, slightly smaller, than the width of the output end of the signal transmission pad. Preferably, the signal output terminal 126 has a length which is comparable to the width of the output end of the signal transmission pad.

With the signal output terminal clamping on the output end of the signal transmission pad, the signal output terminal has an upper portion which projects above the upper surface of the signal transmission pad and a lower portion which projects below the upper surface of the signal transmission pad. For the avoidance of doubt, the terms 'above' and 'below' and other directional terms are relative and are used herein for ease of description and are not intended to be restrictive.

In this example, the signal output terminal is made of a highly conductive metal and is rigid. In other examples, the signal output terminal is made of a resilient flexible and conductive material and can be rigid, semi-rigid or flexible.

The main body of the signal output terminal has an outward-facing outer peripheral wall which delimits the outer boundary of the signal output terminal. This outer peripheral wall defines a distributed signal output surface of the signal output terminal or a distributed signal output surface of the signal collection apparatus. This outer peripheral wall is elongate and generally surrounds the elongate interior compartment.

In the assembled form of the signal collection apparatus 100, the signal output terminals 126 form the free longitudinal ends of the signal collection apparatus 100, as depicted in FIGS. 1A, 1B, 1E and 1F.

In example applications, the example signal collection apparatus 100 is used together with an electronic apparatus, for example, a signal transmitter, a physiological signal processor, an electronic signal processing apparatus, etc., as depicted in FIGS. 2A and 2B. the assembly of the signal collection apparatus 100 and the electronic apparatus 20 forms a physiological signal apparatus 200.

An example electronic apparatus 20 comprises a housing, electronic circuitry disposed inside the housing and a pair of signal input receptacles on the housing, as depicted in FIG. 2A. The example housing is a plastic housing as a convenient example and signal input receptacles are disposed on two lateral sides of the housing. Each of the signal input receptacle comprises a receptacle which is shaped and dimensioned receive the signal output terminal in a closely fitted manner. In order to facilitate closely fitted reception of the signal output terminal, the receptacle is shaped and dimensioned to correspond closely to and match the shape and dimensions of the signal output terminal.

The electronic circuitry of the electronic apparatus 20 includes signal input terminals for receiving physiological signals collected by the signal collection apparatus 100. In this example, the electronic circuitry includes a first signal input terminal for making electrical connection with the signal output terminal of the first ECG signal collection electrode 120A and a second signal input terminal for making electrical connection with the signal output terminal of the second ECG signal collection electrode 120B. The electronic circuitry is mounted or accommodated inside the housing and each one of the signal input terminals includes a conductive portion which is exposed inside the signal input receptacle so that the signal output terminals can establish signal transmission contact with the corresponding signal input terminals. In this example, each signal input terminal includes a resiliently biased pin connector which is resiliently urged and protrudes into the interior of the signal input receptacles so that when the signal output terminals are received inside the signal input receptacles, a firm electrical contact is established between the signal output terminals and the signal input terminals to facilitate transfer of collected physiological signals from the signal collection apparatus 100 to the electronic apparatus 20.

In some embodiments, the electronic circuitry comprises a signal amplifier for amplifying the collected and transferred physiological signals to facilitate subsequent or further signal processing. In some embodiments, the electronic circuitry comprises signal processing means to process the collected and transferred physiological signals for further or immediate processing so that useful information can be provided to a user locally. In some embodiments, the electronic circuitry comprises signal transmission arrangements, for example, a wireless signal transmitter to facilitate outward transmission of collected and/or processed physiological signals and/or data to facilitate external processing.

Referring to FIGS. 2A, 2B, 2C, 2D, 4A, 4B and 4C, the electronic apparatus 20 comprises signal input receptacles on two lateral sides of the housing. Each signal input receptacle is elongate and is shaped and dimensioned to correspond to or to match the shape and dimensions of the signal output terminal 126.

To assemble the physiological signal apparatus 200, a user will insert the signal output terminal of the first ECG signal collection electrode into a first signal input receptacle on the electronic apparatus 20 and to insert the signal output terminal of the second ECG signal collection electrode into a second signal input receptacle on the electronic apparatus 20. To insert an ECG signal collection electrode into a signal input receptacle, the user would need to align the signal output terminal 126 with the signal input receptacle such that the center axis Z-Z' of the signal output terminal 126 is aligned with the center axis of the signal input receptacle. When the two parts are duly aligned, progress of the signal output terminal 126 into the signal input receptacle will force the pin connector of the electronic circuitry to retract resiliently and urged against the outer surface of the signal output terminal 126 to establish a firm and secured signal connection path between the signal output terminal 126 and the signal input terminal of the electronic apparatus 20. When the signal output terminals 126 of the first and second ECJ signal collection electrodes 120A, 120B have been inserted into the signal input receptacles 22 and retained, for example, by friction or by resilient engagement between the resiliently urged pin connector, a loop-shaped physiological signal apparatus 200 as depicted in FIGS. 2A and 2B are formed. In typical applications, the loop shaped physiological signal apparatus 200 is to be formed after an open loop strap 140 is placed to surround the living body.

When the physiological signal apparatus 200 is duly worn on the living body, with the ECG signal collection electrodes 120A, 120B in abutment contact with different body portions, ECG signals will be collected by the ECG signal collection electrodes 120A, 120B and transferred to the electronic apparatus 20 via the signal output terminals and the signal input terminals.

In some embodiments, the signal input terminal inside the signal input receptacle may be a distributed connector. For example, the signal input terminal may include a tubular metallic portion which is to resiliently receive and engage with the signal output terminal to facilitate signal transfer without loss of generality.

An example physiological signal monitoring apparatus 200 comprises a strap 20, a pair of physiological signal collection electrodes mounted on the strap, and an electronic device 40 connected to the strap and the electrodes and comprising electronic circuitry, as depicted in FIGS. 5A and 5B.

The pair of example physiological signal collection electrodes comprises an example first signal collection electrode 220A and an example second signal collection electrode 220B, as depicted in FIGS. 6A1 to 6A4 and 6B1 to 6B4. Each example physiological signal collection electrode 220 comprises a signal collection portion 222, a signal output terminal 226, and a signal transmission bridge 224 interconnecting the signal collection portion and the signal output terminal. The signal collection portion 222, the signal transmission bridge 224 and the signal output terminal 226 are distributed sequentially along a central axis A-A' of the signal collection electrode, and the central axis is also a longitudinal axis which defines a longitudinal direction of the electrode.

The signal collection portion 222 is a signal collection pad comprising a signal collection surface 222' for making abutment contact with the body of a wearer to facilitate collection of physiological signals from the body surface, the signal collection surface is an exposed surface which is parallel to and faces away from the local strap surface on which the signal collection portion 222 is mounted. The signal collection portion 222 has a back surface 222" which is parallel to and in abutment contact with the local strap surface. The signal collection surface 222' has a signal collection area which is large enough to collect physiological signals having a sufficiently large signal magnitude suitable for output and for processing by the electronic device 40. The signal collection surface 222' is generally parallel to the longitudinal axis of the signal collection electrode 220 and the longitudinal axis of the signal output terminal, which is orthogonal to the longitudinal axis of the signal collection electrode 220, the longitudinal axis of the signal collection electrode 220 and the longitudinal axis of the signal output terminal cooperating to define a signal collection plane.

In embodiments such as the present, the signal collection portion comprises an elevated signal collection surface portion which is elevated from a base signal collection surface portion, which surrounds the elevated signal collection surface portion so that the elevated signal collection surface portion defines a signal collection island 2221 surrounded by the base signal collection surface portion 2222.

In embodiments such as the present, the signal collection portion 222, comprising the signal collection island 2221 and the surrounding base portion 2222, are integrally formed from a flexible and conductive moldable soft material such as carbonized rubber or carbonized plastics. The signal collection portion 222 may be made of a flexible and conductive fabric, including woven and non-woven fabrics. The signal collection portion has a generally uniform thickness along its width, the width being defined in a direction orthogonal to the longitudinal direction of the electrode. Where the signal collection portion has a signal collection island 2221, the signal collection island 2221 is a signal collection pad having a generally uniform thickness and a generally uniform width, and the surrounding base portion 2222 has the same or another generally uniform thickness and width.

The signal transmission bridge 224 is to facilitate conduction of electrical signals between the signal collection portion 222 and the signal output terminal 226. In example applications, physiological signals, in the form of low-frequency electrical pulses collected by the signal collection portion, are to be transmitted forwardly to the signal transmission bridge 224 and then forwardly to the signal output terminal 226 for ultimate output. The electrical signals are to travel in the longitudinal direction of the electrode 220, the longitudinal direction defining an electrical conduction path of the shortest distance between the signal collection portion 222 and the signal output terminal 226. The example signal transmission bridge 224 is made of a flexible and conductive material and comprises a flexible bridging portion which extends between the signal collection surface and the signal output terminal. The bridging portion comprises a body-facing surface which is parallel to the signal collection surface and an outward-facing surface which faces away from the wearer during use. The bridging portion continues electrically and physically from the forward longitudinal end of the signal collection portion and the signal output terminal is connected to the forward longitudinal end of the signal transmission bridge 224. In embodiments such as the present, the signal collection portion 222 and the signal transmission bridge 224 are integrally formed, for example, molded, from the same material. The signal collection portion 222 and the signal transmission bridge 224 may have the same width, although in some embodiments the signal transmission bridge 224 has a smaller width than the signal collection portion 222. The signal transmission bridge 224 may have a width which is 65-85% of the width of the signal collection portion 222.

Each of the signal collection portion 222 and the signal transmission bridge 226 is elongate and has a low-profile form factor. A low-profile form factor herein means having a width which is substantially larger than its thickness. The signal collection pad (or pad in short) and the bridge portion resembles the form factor of a strip of an elongate tab. The example pad and bridge portion have an example width-to-thickness ratio of $\geq 3:1$, $4:1$ or $5:1$. In example embodiments, the signal collection portion and the signal transmission bridge are integrally formed, for example, from a flexible and resilient conductive material such as carbonized rubber so that the signal collection electrode 220 is in the form of an elongate strip or tab. In example embodiments such as the present, the pad and the bridge portion have substantially same or uniform thickness along the longitudinal axis.

The strap 20 has a first longitudinal end 22A, a second longitudinal end 22B and an intermediate portion 22 interconnecting the first and second longitudinal ends 22A, 22B, and the intermediate portion 22 defines an effective length of the strap along its center longitudinal axis. The first signal collection electrode 220A is mounted on the intermediate portion 22 of the strap 20, with its signal output terminal 226 proximal and terminating the first longitudinal end 22A. The signal output terminal 226 extends orthogonally to the longitudinal axis of the signal collection electrode 220A and parallel to the signal collection surface to encapsulate the signal output end portion of the first signal collection electrode 220A. The signal output terminal 226 encapsulates the entire width of the signal output end portion of the first signal collection electrode 220A as depicted in FIGS. 6A1 to 6A4, or a substantial width portion thereof. The signal collection portion 222 of the first signal collection electrode 220A is mounted on the intermediate portion 22 of the strap and extends longitudinally away from the first longitudinal end 22A and longitudinally towards the second longitudinal end 22B in a direction opposite to the direction extension of the second signal collection electrode 220B. The example signal output terminal 226 has a generally C-shaped cross-section along its length to form a C-shaped clamp and the signal output end portion of the signal collection electrode 220A, 220B is retained inside the internal compartment of the C-shaped clamp and is compressively engaged so that good electrical contact is made between the signal output end portion and the signal output terminal 226 to facilitate effective and efficient physiological signal transfer.

Similarly, the second signal collection electrode 220B is mounted on the intermediate portion 22 of the strap 20, with its signal output terminal 226 proximal and terminating the second longitudinal end 22B, and with the signal output terminal 226 extending orthogonally to the longitudinal axis of the signal collection electrode 220B and parallel to the signal collection surface to encapsulate the signal output end portion of the second signal collection electrode 220B. The signal output terminal 226 encapsulates the entire width of the signal output end portion of the second signal collection electrode 220B as depicted in FIGS. 6B1 to 6B4, or a substantial width portion thereof. The signal collection portion 222 of the second signal collection electrode 220B is mounted on the intermediate portion 22 of the strap and extends longitudinally away from the second longitudinal end 22B and longitudinally towards the first longitudinal end 22A in a direction opposite to the direction extension of the first signal collection electrode 220A.

In embodiments such as the present, each one of the first and second longitudinal ends 22A, 22B is a free end so that the strap 20 is convertible between an open-ended belt and a closed loop when in cooperation with a strap-ends connector (or strap connector in short). The strap 20 may be made of fabrics, for example, a breathable, non-conductive and resiliently stretchable fabric, including woven and non-woven fabrics. The strap 20, or more specifically the immediate portion 22 of the strap, is intended to function as an insulated carrier or an insulated substrate of the signal collection electrodes 220A, 220B and the associated electronic device. The intermediate portion 22 of the strap 20 provides partial physical shielding to the back surface of the signal collection electrode, and more specifically to the signal collection pads and the bridge portions so that the pads and bridge portions of the signal collection electrodes 220A, 220B are visually hidden when viewed towards the user with the electronic device in sight. In addition, the intermediate portion 22 of the strap is to mechanically shield the pads and the bridge portions from at least a substantial portion of the longitudinally elongating tension to promote durability and reliability, since the end of the electrode distal from the signal output terminal is floatingly carried on the intermediate portion and is not fastened to a longitudinal end of the strap. The term floatingly herein means portion of the intermediate portion of the strap between the distal ends of the electrodes is more elongate-able then the portions which are in abutment with the pads and the bridging portions.

The strap 20 and the pair of signal collection electrodes 220A, 220B mounted thereon collectively form a signal collection strap which is also a signal collection apparatus 230. In embodiments such as the present, the signal collection apparatus 230 is a passive apparatus having passive components for passive collection of physiological signals. The signal collection apparatus is to cooperate with an electronic device to facilitate signal processing, data storage and/or for on-ward transmission of signals or data. In example embodiments such as the present, the electronic device is configured as a strap-ends connector which converts the open-ended strap apparatus into a closed-loop signal collection and processing apparatus.

The electronic device 40 which is to function as a strap-ends connector is also a physiological signal hub (signal hub in short). Physiological signals collected by the first and second electrodes 220A, 220B are to flow into the electronic device 40 and the electronic circuitry thereof is to process the collected signals according to the design of the electronic circuitry. The electronic circuitry may comprise signal processing circuitry, data storage circuitry and/or data transmission circuitry for onward transmission of raw or processed data.

In example embodiments such as the present, the electronic device 40 and the electrodes 220A, 220B are in physical and electrical connection so that collected physiological signals are to flow into the electronic circuitry and processed by circuitry therein.

The electronic device 40 comprises a rigid main housing 42, a first hub terminal 44A on a first side of the main housing forming a first retention terminal and a second hub terminal 44B on a second side of the main housing forming a second retention terminal, the second hub terminal being on a diametrically opposite side of the of first hub terminal, as depicted in FIGS. 5A, 5B and 7A1-7A4. The main housing 42 defines a hollow internal compartment inside which the electronic circuitry is housed. The first hub terminal 44A comprises a first retention device for retention of the first signal output terminal and a first signal input terminal of the signal hub. The second hub terminal 44B comprises a second retention device for retention of the second signal output terminal and a second signal input terminal of the signal hub. During normal use when the assembly in a physiological signal collection mode and when physiological signals are to be collected from a user or wearer, the signal collection apparatus is in an anchored mode and is anchored on the electronic device 40 as a signal hub, with the first signal output terminal anchoring on the first retention terminal and with the second signal output terminal anchoring on the second retention terminal. When in the anchored mode, the first signal output terminal 226 of the first signal collection electrode 220A is mechanically retained by the first retention device of the signal hub and is prevented from separation in the longitudinal direction even when the first signal output terminal 226 is subject to a longitudinal separation force, and the second signal output terminal 226 of the second signal collection electrode 220B is mechanically retained by the second retention device of the signal hub and is prevented from separation in the longitudinal direction even when the second signal output terminal 226 is subject to a longitudinal separation force opposite to the longitudinal separation force on the first signal collection electrode 220A.

In embodiments such as the present, the output terminal 226 is for snap-fit latched engagement with the first retention device of the hub terminals 44A, 44B. To facilitate snap-fit latched engagement, the output terminal 226 and the hub terminals 44A, 44B respectively comprise complementary snap-fit latching components and/or have complementary shapes and dimensions to facilitate closely-fitted reception and to enhance snap-fit latching.

In embodiments such as the present, the output terminal 226 and its corresponding retention terminal on the hub terminals 44A, 44B are relatively movable along a traverse direction to the strap longitudinal axis so that the output terminal 226 can move into or out of mechanical engagement with a corresponding retention terminal.

When the signal collection apparatus 230 is in anchored engagement with the signal hub 40, the signal collection assembly comprising the signal collection apparatus 230 and the signal hub 40 is in the configuration of a closed loop. Therefore, the first retention terminal also functions as a first anchoring terminal and the second retention terminal also functions as a second anchoring terminal. The intermediate portion 22 of the strap 20 is in the form of an elastic band and is flexible, resilient and stretchable or elongate-able in the longitudinal direction. When in normal use, the strap assembly comprising the signal collection apparatus and the signal hub is worn as a closed loop on the body of the user, with the intermediate portion of the strap subject to an elongating tension in the longitudinal direction and with the signal collection surfaces of the signal collection electrodes in abutment contact with spaced apart naked body portions of the user. When in the normal use configuration, the signal collection surfaces of the signal collection electrodes 220A, 220B will be in compressive physical to establish electrical contact with the respective exposed body surfaces of the spaced apart body portions of the user. The length of the intermediate portion of the strap is adjusted according to the size of the user, or more specifically the size of the body portion of the user, in order to produce an appropriate level of radial compressive tension for effective electrical signal collection from the exposed body surface of the user. The strap may be woven from elastic yarns to provide elasticity and breathability. To enhance comfort and breathability, the signal collection portion and/or the signal transmission portion may be perforated.

The signal output terminal 226 of the signal collection electrode 220 comprises a main body and a receptacle. The main body is elongate and extends along a longitudinal direction between a first longitudinal end and a second longitudinal end, the longitudinal direction being defined by a longitudinal axis which is also a center axis of the main body, and the longitudinal direction of the main body is orthogonal or substantially orthogonal to the longitudinal direction of the signal collection electrode 220. The main body has an outer peripheral wall defining an outer peripheral surface and interconnecting the first and second longitudinal ends.

The receptacle comprises an open channel for receiving a signal output end portion 2241 of the signal collection electrode 220. The open channel is elongate, extends between the first and second longitudinal ends, and has a channel axis which is a center axis of the channel. In example embodiments such as the present, the channel axis is parallel to the longitudinal axis of the main body. The open channel has an entry aperture formed on the first longitudinal end and an electrode bridge passage aperture formed on the outer peripheral surface. The electrode bridge passage aperture is defined by a bridge passage window which is formed on the outer peripheral surface. The bridge passage window has a width which is wider, for example slightly wider, than the width of the signal output end portion of the signal collection electrode and a depth which is larger, for example slightly larger, than the thickness of the signal output end portion of the signal collection electrode. In general, the bridging portion passage window defines a transversal aperture which is a window aperture having a clearance or clearance dimensions sufficient to permit slide entry of the portion of the bridging portion which is immediately proximal the signal output end portion into the bridge passage window by moving or sliding in a lateral or transversal direction (which is parallel to the longitudinal direction of the main body) while preventing through-passage of the signal output terminal across the window by moving in the longitudinal direction of the signal collection electrode (which is orthogonal to the longitudinal direction of the main body).

In embodiments such as the present, the open channel extends between a first entry aperture which is formed on the first longitudinal end and a second entry aperture which is formed on the second longitudinal end. In addition, the aperture defined by the bridging portion passage window is a through aperture extending between the first and second longitudinal ends. When the aperture is a through aperture on the outer peripheral surface of the main body, the portion of the bridging portion which is immediately proximal the signal output end portion into the bridge passage window can slide into the anchoring terminal in either, that is opposite, transversal directions.

The main body of the signal output terminal 226 comprises an upper body portion, a lower body portion and a forward body portion interconnecting the upper and lower body portions. Each of the body portions is elongate and extends in the longitudinal direction of the main body and the body portions cooperate to define the open channel and the window aperture. The upper body portion has an upward-facing upper surface which is an outer surface in abutment contact with the anchoring terminal and a downward-facing lower surface which is an interior surface, the downward-facing surface defining a ceiling portion of the open channel. The lower body portion has an upward-facing upper surface which is an interior surface defining a floor portion of the open channel and a downward-facing lower surface which is an outer surface in abutment contact with the anchoring terminal. The forward body portion forms the forward (or forward-most) end of the signal collection electrode and comprises a forward-facing surface which is in abutment contact with the anchoring terminal and a rearward-facing surface which is opposite facing and proximal the longitudinal end of the bridging portion. The forward body portion orthogonally intercepts the center longitudinal axis of the signal collection electrode. The upper body portion, the lower body portion and the forward body portion cooperate to define an internal compartment for receiving a signal output end portion of the signal collection electrode 220.

In embodiments such as the present, the upward-facing surface of the upper body portion is an upper surface of the signal output terminal and is a convex surface with respect to the center axis of the main body, the downward-facing surface of the lower body portion is a lower surface of the signal output terminal and is a convex surface with respect to the center axis of the main body, and the forward-facing surface of the forward body portion is the forward-most surface of the signal collection electrode and is a convex surface with respect to the center axis of the main body. Optionally, the curved surfaces of the outer surfaces of the body portions of the main body share a common radius of curvature with respect to the center longitudinal axis of the main body, so that the main body is a cylindrical body, which means a generally and not necessarily absolutely cylindrical body herein. In some embodiments, the main body has an oval, square or polygonal cross section.

The upper body portion of the signal output terminal projects upwardly to protrude above the upper major surface of the signal transmission bridge while the lower body portion of the signal output terminal projects downwardly to protrude below the lower major surface of the signal transmission bridge, the upper and lower major surface cooperating to define thickness of the bridging portion of the signal transmission bridge.

A forward longitudinal end portion of the signal transmission bridge or bridging portion is received inside the open channel for forward transmission of electrical signals collected by the signal collection electrode to the electronic device connected to the pair of signal collection electrodes. The forward longitudinal end of the portion of the signal transmission bridge is retained inside the open channel, for example, by compressive clamping force exerted by cooperation of the upper and lower body portions and/or by means of fastening means.

In example, embodiments, the fastener means comprises a screw or a plurality of screws which penetrates through the upper or lower body portion of the signal output terminal in a direction orthogonal to both the main body center axis and the electrode center axis to engage with the forward longitudinal end portion of the signal transmission bridge, which is a signal output end portion of the signal collection electrode.

In some embodiments, the upper body portion and/or the lower body portion of the signal output terminal is/are in compressive engagement with the signal transmission bridge to facilitate efficient signal transfer between the signal collection electrode and the electronic device.

In some embodiments, the forward end of the signal collection electrode is mounted on the strap end as a substrate, in which case at least the upper major surface of the signal transmission bridge, which faces the wearer during use, is in compressive engagement with the upper body portion of the signal output terminal.

In example embodiments, the length of the main body is comparable to or approximately equal to the width of the bridging portion or the width of the forward longitudinal end of the portion of the signal transmission bridge.

In example embodiments such as the present, the main body is made of a highly conductive metal such as copper, copper alloy, nickel and/or chromium alloy such as a nickel or chromium steel.

In example embodiments such as the present, the main housing 42 of the electronic device 40 comprises an upper housing portion and a lower housing portion which are made of hard plastics and are fastened together to form a watertight housing to define an internal circuitry compartment for housing the electronic circuitry. The man housing 42 comprises a peripheral wall which surrounds the internal compartment, as depicted in FIGS. 7A1 to 7A4.

The hub terminal 44A, 44B of the electronic device 40 comprises a hub terminal housing which defines an output terminal receptacle 44A2, 44B2 for mechanical retention of and electrical connection with the signal output terminal 226 of the signal collection electrode. The hub terminal housing projects laterally outwards from a lateral side of the main housing 42 and the hub terminals 44A, 44B are on opposite diametrical sides of the circuitry compartment, the opposite diametrical sides being on the longitudinal axis of the signal collection electrodes. The hub terminal is a lateral extension of the main housing 42 of the electronic device and defines an output terminal receptacle for receiving the signal output terminal 226 of a signal collection electrode 220A, 220B.

The receptacle comprises a channel for receiving the signal output terminal 226, a strap passage aperture 44A4, 44B4 to permit a portion of the strap 22 to pass through the receptacle, and an entry aperture to permit the signal output terminal 226 to enter into the receptacle, as depicted more clearly in FIGS. 8A1 to 8A3. The example channel of the hub terminal 44A, 44B is an open channel, with entry aperture defining an entry end of the open channel, so that the signal output terminal 226 can slide into the receptacle along the longitudinal direction of the signal output terminal 226 and through entry at the entry aperture on a longitudinal end of the channel. The channel has a center axis which is orthogonal to the longitudinal axis of the signal collection electrode 220A, 220B. The strap passage aperture is defined by a pair of aperture-defining walls each having an edge parallel to the channel center axis to define an elongate strap passage aperture. The dimensions of the strap passage aperture, in particular the height, are large enough to permit through-passage of the strap in the longitudinal direction but are not large enough to permit through-passage of the signal output terminal 226 in the longitudinal direction. The receptacle has an internal compartment having dimensions comparable to that of the signal output terminal 226 for closely fitted reception. The receptacle has internal walls which defines the open channel. Exposed electrical contacts for making electrical contact with the signal collection electrode 220A, 220B are formed on and/or protruding radially inwards from internal walls.

When the signal output ends of the signal collection apparatus 230 are received inside the hub terminals 44A, 44B, the longitudinal axis of the output signal terminal is aligned (that is coaxial) with the center axis of the output terminal receptacle 44A2, 44B2. The signal output end portion of the signal collection apparatus 230, comprising longitudinal end portions of the signal collection electrode 220A, 220B and the strap 22, is mechanically fastened to the signal output terminal 226 by fastening means. The fastening means penetrates through the signal output end portion of the signal collection apparatus 230 and anchors on the upper and lower body portions of the signal output terminal 226, as depicted in FIGS. 8A1 and 8A2. The example fastener means comprises a pair of screws, and each screw has a shank which extends orthogonally through the signal output end portion of the signal collection apparatus 230. The signal output end portion of the signal collection apparatus 230 occupies almost all the space inside the hub terminals 44A, 44B to ensure good electrical contact with the exposed electrical contacts 446 inside the hub terminals 44A, 44B and the exposed electrical contacts 446 are in electrical connection with the electronic circuitry of the electronic device 40.

A localized indentation or dent is formed on the outer peripheral surface of the main body of the signal output terminal 226. In the present example embodiment, the den is formed on the middle of the main body and the exposed resilient contact 446 comprises a rounded contact peak which projects upwardly from a lower body portion of the output terminal receptacle 44A2, 44B2 to complementarily engage with the dent on the signal output terminal 226.

Referring to FIG. 8A3, exposed resilient contacts 446 are formed inside the receptacle and protrudes radially inwards to resilient engage with the signal output terminal 226 to facilitate good mechanical and electrical contact by friction engagement for efficient signal transfer. The contact 446 is formed from a metal strip which is bent into the shape having a wider base in abutment with the output terminal receptacle 44A2, 44B2 and a round contact peak projecting radially into the open channel and elevated from an inner base surface of the output terminal receptacle 44A2, 44B2.

In embodiments such as the present, the signal collection electrodes are for collecting ECG signals and the signal collection surface has an example length of between 8 cm-20 cm and a width of between 1.5 cm-2.5 cm, with rounded corners at the longitudinal ends. The bridging portion has an example length of between 5 cm-12 cm and a width of between 1.0-2.2 cm.

In embodiments such as the present, the apparatus and the electrodes are for collecting and processing low-frequency electrical pulses such as ECG pulses or muscle contraction pulses having a frequency range of between tens to hundreds or cycles. Of course, electronic circuitry for processing higher-frequency components of the physiological signals may be included without loss of generality.

In some embodiments, the signal collection portion 222, the signal transmission bridge 224 and the signal output terminal 226 are integrally formed as a single piece, for example, from conductive rubber or soft metal or conductive fabrics.

While the present disclosure has been explained with reference to example or embodiments, it should be appreciated that the embodiments are only described to illustrate the invention and are not meant for restricting the scope of invention. For example, while a swim monitor strap has been illustrated as an example, a strap of the present invention could be used for running or other activities without loss of generality.

The invention claimed is:
1. A physiological signal collection electrode comprising a signal collection portion, a signal output terminal and a signal transmission portion interconnecting the signal collection portion and the signal output terminal, wherein the signal collection portion comprises a signal collection pad which is configured for collecting ECG signals and on which a signal collection surface is defined;

wherein the signal transmission portion comprises a signal transmission pad which extends along a longitudinal axis between a forward end which is in abutment with the signal output terminal and a rearward end which is in abutment with the signal collection pad, the signal collection pad and the signal transmission pad being integrally formed of a conductive elastomer;

wherein the signal collection surface is configured for making abutment contact with a physiological signal surface of a physiological signal source whereby physiological signals are collected, and the signal transmission pad has a signal output portion on the forward end;

wherein the signal output terminal is configured to output physiological signals collected from the physiological signal surface and comprises a rigid metallic body which encapsulates the signal output portion of the signal transmission pad to form a signal output surface of the electrode, wherein the rigid metallic body comprises a first body portion, a second body portion, and a third body portion interconnecting the first body portion and the second body portion, and wherein the metallic body is attached to the signal output portion by compressive cooperation between the first body portion and the second body portion, and wherein the third portion projects forward of the signal transmission pad to define a forward end of the electrode.

2. The physiological signal collection electrode of claim 1, wherein the first body portion comprises a first interior wall portion and a first exterior wall portion, the second body portion comprises a second interior wall portion and a second exterior wall portion, and the third body portion comprises a third interior wall portion and a third exterior wall portion;

wherein the third interior wall portion interconnects the first interior wall portion and the second interior wall portion, and the third exterior wall portion interconnects the first exterior wall portion and the second exterior wall portion;

wherein the first interior wall portion, the second interior wall portion and the third interior wall portion cooperate to define a receptacle inside which the signal output portion is received; and wherein the first interior wall portion and the second interior wall portion cooperate to clamp the signal output portion in electrical contact with the metallic body of the signal output terminal, and the third interior wall portion is forward of the forward end of the signal transmission pad.

3. The physiological signal collection electrode of claim 2, wherein the first exterior wall portion has a first exterior surface, the second exterior wall portion has a second exterior surface, and the third exterior wall portion has a third exterior surface interconnecting the first exterior surface and the second exterior surface;

wherein the first exterior surface, the second exterior surface and the third exterior surface cooperate to define the signal output surface of the electrode, and wherein the signal output surface of the electrode surrounds the receptacle and the signal output portion of the signal transmission pad.

4. The physiological signal collection electrode of claim 3, wherein the signal output portion of the signal transmission pad has a first surface, a second surface, and a third surface which is a forward-end surface interconnecting the first surface and the second surface;

wherein the signal collection surface defines a body-facing direction which is orthogonal to the longitudinal axis, wherein the first surface of the signal transmission pad has a facing direction which is same as the body-facing direction, and the second surface has a facing direction which is opposite to the body-facing direction; and wherein the signal output surface of the electrode is a continuous surface which extends to surround the first surface, the second surface and the third surface of the signal output portion.

5. The physiological signal collection electrode of claim 4, wherein the signal output surface of the electrode is a convexly curved surface which surrounds the first surface, the second surface and the third surface of the signal output portion of the signal transmission pad.

6. The physiological signal collection electrode of claim 4, wherein the first exterior surface, the second exterior surface and the third exterior surface of the signal output terminal respectively defines a first convex surface, a second convex surface, and a third convex surface; and wherein the first convex surface, the second convex surface, and the third convex surface cooperate to define a convexly curved signal output surface of the electrode which surrounds the signal output portion of the signal transmission pad.

7. The physiological signal collection electrode of claim 6, wherein the first convex surface has a facing direction which is same as the body-facing direction, and the second convex surface has a facing direction which is opposite to the body-facing direction; and the third convex surface has a facing direction which is orthogonal to the body-facing direction.

8. The physiological signal collection electrode of claim 7, wherein the third convex surface projects forward of the signal transmission pad and defines a convex forward end of the electrode.

9. The physiological signal collection electrode of claim 6, wherein the first interior wall portion, the second interior wall portion, and the third interior wall portion cooperate to define a groove which is delimited by the receptacle;

wherein the groove has a groove axis which is orthogonal to the body-facing direction, an entry aperture which is configured to permit entry and withdrawal of the signal output portion and which extends along a direction that is parallel to the groove axis, and a closed forward end which is distal from the entry aperture;

wherein the groove and the entry aperture are defined by cooperation of the first interior wall portion and the second interior wall portion, and the closed forward end is defined by the third interior wall portion.

10. The physiological signal collection electrode of claim 9, wherein the first surface of the signal transmission pad is in compressive contact with the first interior wall portion, and the second surface of the signal transmission pad is in compressive contact with the second interior wall portion.

11. The physiological signal collection electrode of claim 4, wherein the metallic body has a prism shape and a center axis which is a prism axis of a prism having an outer surface which surrounds the prism axis, wherein the signal output surface of the electrode resembles the outer surface of a prism, and wherein the center axis of the metallic body passes through the signal output portion of the signal transmission pad.

12. A physiological signal collection apparatus comprising a set of physiological signal collection electrodes which comprises at least one physiological signal collection electrode, and an electronic device for processing physiological signals collected by the physiological signal collection electrode;
- wherein the physiological signal collection electrode comprises a signal collection portion, a signal output terminal and a signal transmission portion interconnecting the signal collection portion and the signal output terminal defining a signal output surface,
- wherein the signal collection portion comprises a signal collection pad on which a signal collection surface is defined;
- wherein the signal transmission portion comprises a signal transmission pad which extends along a longitudinal axis between a forward end which is in abutment with the signal output terminal and a rearward end which is in abutment with the signal collection pad, the signal collection pad and the signal transmission pad being integrally formed of a conductive elastomer;
- wherein the signal collection surface is for making abutment contact with a physiological signal surface and is parallel to the longitudinal axis, the signal collection surface defining a body-facing direction which is orthogonal to the longitudinal axis;
- wherein the signal transmission pad has a signal output portion on the forward end, the signal output portion of the signal transmission pad having a first surface, a second surface, and a third surface which is a forward-end surface interconnecting the first surface and the second surface;
- wherein the first surface of the signal transmission pad has a facing direction which is same as the body-facing direction, and the second surface has a facing direction which is opposite to the body-facing direction; and
- wherein the signal output surface of the electrode is a convexly curved metallic surface which extends to surround the first surface, the second surface and the third surface of the signal output portion of the signal transmission pad;
- wherein the electronic device comprises a housing, a terminal receptacle for receiving the signal output terminal of an electrode, and electronic circuitry for processing physiological signals collected by the physiological signal collection electrode;
- wherein the terminal receptacle is configured for closely-fitted reception of the signal output terminal and comprises an internal wall which surrounds the signal output terminal; and
- wherein a set of electrical contacts comprising at least one resilient electrical contact is disposed in the terminal receptacle and exposed through the internal wall for making signal interconnection between the signal output terminal and the electronic circuitry of the electronic device.

13. The physiological signal collection apparatus of claim 12, wherein the signal output terminal is detachably mounted on the signal transmission pad, wherein the terminal receptacle is configured for slide entry of the signal output terminal in a direction which is orthogonal to the longitudinal axis and orthogonal to the body-facing direction, and wherein the terminal receptacle comprises a latching arrangement which is configured to enter into snap-fitted latching engagement with the signal output terminal when the signal output terminal is fully inside the terminal receptacle.

14. The physiological signal collection apparatus of claim 13, wherein the signal output terminal comprises a rigid metallic body which encapsulates the signal output portion of the signal transmission pad,
- wherein the rigid metallic body comprises a first body portion, a second body portion, and a third body portion interconnecting the first body portion and the second body portion,
- wherein the metallic body is attached to the signal output portion by cooperation between the first body portion and the second body portion, and wherein the third portion projects forward of the signal transmission pad to define a forward end of the electrode;
- wherein the first body portion comprises a first convex exterior wall portion, the second body portion comprises a second convex exterior wall portion, and the third body portion comprises a third convex exterior wall portion; and
- wherein the first convex exterior wall portion, the second convex exterior wall portion and the third convex exterior wall portion cooperate to form a continuous convexly curved metallic signal output surface of the electrode.

15. The physiological signal collection apparatus of claim 14, wherein the apparatus comprises an extendable strap for wearing by a user and the electrode is mounted on the extendable strap;
- wherein the signal output portion of the signal transmission pad is compressively retained inside the metallic body by a set of threaded fasteners in cooperation with the first body portion and the second body portion; and
- wherein the set of threaded fasteners is operable to adjust the separation spacing between the first body portion and the second body portion whereby the signal output portion of the signal transmission pad is clamped by cooperation of the first body portion and the second body portion.

16. A physiological signal collection electrode comprising a signal collection portion, a rigid metallic body which is configured as a signal output terminal, and a signal transmission portion interconnecting the signal collection portion and the signal output terminal,
- wherein the signal collection portion comprises a signal collection pad on which a signal collection surface is defined;
- wherein the signal transmission portion comprises a signal transmission pad which extends along a longitudinal axis between a forward end which is in abutment with the signal output terminal and a rearward end which is in abutment with the signal collection pad, the signal collection pad and the signal transmission pad being integrally formed of a conductive elastomer;
- wherein the signal collection surface is configured for making abutment contact with a physiological signal surface of a physiological signal source whereby physiological signals are collected, and the signal transmission pad has a signal output portion on the forward end;
- wherein the signal output terminal is configured to output physiological signals collected from the physiological signal surface and comprises a rigid metallic body which encapsulates the signal output portion of the signal transmission pad to form a signal output surface of the electrode,
- wherein the rigid metallic body comprises main body including a first body portion, a second body portion, a third body portion interconnecting the first body portion and the second body portion, and an outward-facing outer peripheral wall which defines a distributed signal output surface; and wherein the first body portion and the second body portion of the rigid metallic body are in compressive engagement with the forward end of the signal transmission pad to facilitate efficient physiological signal transfer between the signal transmission pad and the signal output terminal.

17. The physiological signal collection electrode of claim 16, wherein the first body portion has an upper internal boundary wall, the second body has a lower internal boundary wall, and the third body portion has an internal peripheral wall interconnecting the upper internal boundary wall and the lower internal boundary wall;

wherein the first body portion projects rearwardly from the internal peripheral wall and has a rear end which is a free end overhanging the third body portion, wherein the second body portion projects rearwardly from the internal peripheral wall and has a rear end which is a free end overhanging the third body portion, wherein the first body portion and the second body portion are separated by a separation spacing, and wherein the rear ends of the first body portion and the second body portion are resiliently movable with respect to the internal peripheral wall towards each other.

18. The physiological signal collection electrode of claim 16, wherein the signal output portion of the signal transmission pad is compressively retained inside the receptacle by a set of fasteners in cooperation with the first body portion and the second body portion, and wherein the set of fasteners is operable to adjust the separation spacing between the first body portion and the second body portion.

19. The physiological signal collection electrode of claim 18, wherein the set of fasteners comprises at least one threaded fastener which passes through the signal transmission pad to extend between the first body portion and the second body portion.

20. The physiological signal collection electrode of claim 18, wherein the signal output portion of the signal transmission pad is detachably retained on the signal output terminal by the set of fasteners.

* * * * *